(12) United States Patent
Subramanian et al.

(10) Patent No.: US 6,934,032 B1
(45) Date of Patent: Aug. 23, 2005

(54) COPPER OXIDE MONITORING BY SCATTEROMETRY/ELLIPSOMETRY DURING NITRIDE OR BLOK REMOVAL IN DAMASCENE PROCESS

(75) Inventors: Ramkumar Subramanian, Sunnyvale, CA (US); Steven C. Avanzino, Cupertino, CA (US); Bharath Rangarajan, Santa Clara, CA (US); Bhanwar Singh, Morgan Hill, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 144 days.

(21) Appl. No.: 10/261,514

(22) Filed: Sep. 30, 2002

(51) Int. Cl.[7] .................. G01N 21/55; H01L 21/66; C23F 1/18
(52) U.S. Cl. .............. 356/445; 356/369; 356/448; 250/225; 438/16; 156/345.13; 216/60
(58) Field of Search .................. 356/369, 630, 356/445, 446, 16; 250/225, 559.09, 559.27; 438/16; 700/109, 121; 702/155; 156/345.13; 216/60

(56) References Cited

U.S. PATENT DOCUMENTS

| | | | | |
|---|---|---|---|---|
| 5,896,294 A * | 4/1999 | Chow et al. | ................ | 700/121 |
| 5,928,532 A * | 7/1999 | Koshimizu et al. | ......... | 356/316 |
| 5,986,747 A * | 11/1999 | Moran | ......................... | 356/316 |
| 6,051,496 A * | 4/2000 | Jang | ............................. | 438/687 |
| 6,195,594 B1 * | 2/2001 | Shah et al. | .................... | 700/97 |
| 6,204,168 B1 * | 3/2001 | Naik et al. | .................. | 438/638 |
| 6,228,771 B1 * | 5/2001 | Allers | ........................ | 438/693 |
| 6,261,953 B1 * | 7/2001 | Uozumi | ...................... | 438/687 |
| 6,292,265 B1 * | 9/2001 | Finarov et al. | ............. | 356/630 |
| 6,372,291 B1 * | 4/2002 | Hua et al. | ................... | 438/763 |
| 6,417,112 B1 * | 7/2002 | Peyne et al. | ................ | 438/754 |
| 6,475,909 B2 * | 11/2002 | Uozumi | ...................... | 438/678 |
| 6,514,865 B1 * | 2/2003 | Evans | ......................... | 438/14 |
| 6,517,413 B1 * | 2/2003 | Hu et al. | ........................ | 451/6 |
| 6,525,829 B1 * | 2/2003 | Powell et al. | ................ | 356/630 |
| 6,579,730 B2 * | 6/2003 | Li et al. | ........................ | 438/14 |
| 6,586,342 B1 * | 7/2003 | Mayer et al. | ............... | 438/754 |
| 6,594,025 B2 * | 7/2003 | Forouhi et al. | ............. | 356/630 |
| 6,633,831 B2 * | 10/2003 | Nikoonahad et al. | ....... | 702/155 |
| 6,667,239 B2 * | 12/2003 | Saka et al. | ................... | 438/692 |
| 6,679,761 B1 * | 1/2004 | Sunahara et al. | ........... | 438/691 |
| 6,736,926 B2 * | 5/2004 | Chopra et al. | ......... | 156/345.13 |
| 6,825,562 B2 * | 11/2004 | Naik et al. | .................. | 257/758 |
| 2002/0186381 A1 * | 12/2002 | Subrahmanyan et al. | ... | 356/630 |

* cited by examiner

Primary Examiner—Michael P. Stafira
Assistant Examiner—Juan D. Valentin, II
(74) Attorney, Agent, or Firm—Amin & Turocy, LLP

(57) ABSTRACT

A system and methodology for monitoring and/or controlling a semiconductor fabrication process is disclosed. Scatterometry and/or ellipsometry based techniques can be employed to facilitate providing measurement signals during a damascene phase of the fabrication process. The thickness of layers etched away during the process can be monitored and one or more fabrication components and/or operating parameters associated with the fabrication component(s) can be adjusted in response to the measurements to achieve desired results, such as to mitigate the formation of copper oxide during etching of a copper layer, for example.

14 Claims, 17 Drawing Sheets

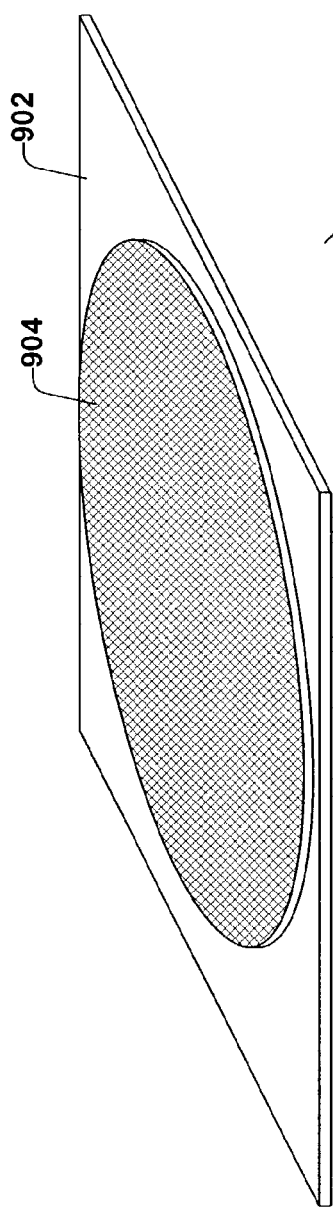
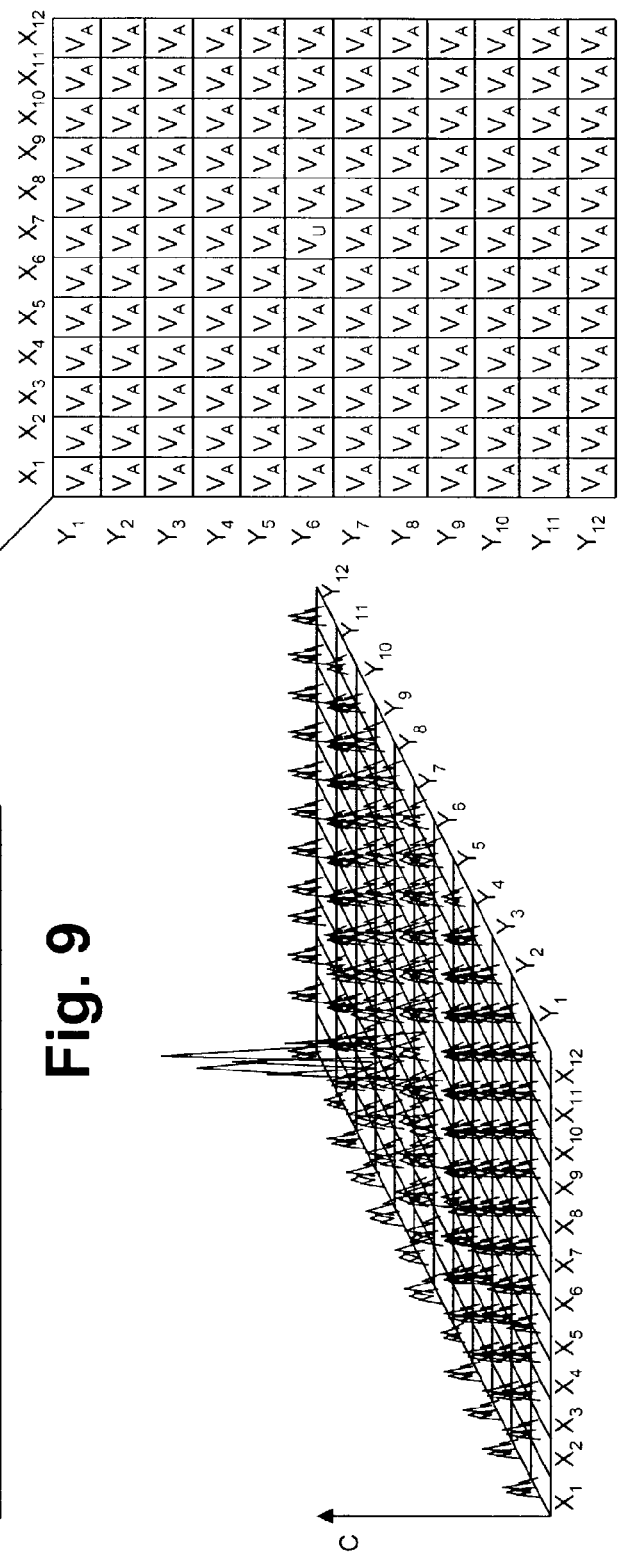
Fig. 9
Fig. 10
Fig. 11

COPPER OXIDE MONITORING BY SCATTEROMETRY/ELLIPSOMETRY DURING NITRIDE OR BLOK REMOVAL IN DAMASCENE PROCESS

FIELD OF THE INVENTION

The present invention generally relates to semiconductor processing, and in particular to a system and methodology for monitoring and/or controlling stages, such as an etching stage in a damascene phase, of a semiconductor fabrication process.

BACKGROUND OF THE INVENTION

In the semiconductor industry, there is a continuing trend toward higher device densities. To achieve these high densities, there has been and continues to be efforts toward scaling down device dimensions (e.g., at submicron levels) on semiconductor wafers. In order to accomplish such high device packing density, smaller and smaller feature sizes are required in integrated circuits (ICs) fabricated on small rectangular portions of the wafer, commonly known as dies. This may include the width and spacing of interconnecting lines, spacing and diameter of contact holes, the surface geometry such as corners and edges of various features as well as the surface geometry of other features. The dimensions of and between features can be referred to as critical dimensions (CDs). Reducing CDs, and reproducing more accurate CDs facilitates achieving higher device densities through scaled down device dimensions and increased packing densities.

The process of manufacturing semiconductors or ICs typically includes numerous steps (e.g., etching, developing), during which hundreds of copies of integrated circuits may be formed on a single wafer, and more particularly on each die of a wafer. In many of these steps, material is overlayed or removed from existing layers at specific locations to form electrically active regions and desired elements of the integrated circuit. Metallization is one important aspect of semiconductor fabrication. Metallization or damascene is the process of interconnecting individual devices and components on a wafer and/or on one or more die on a wafer. Typically, damascene processes involve forming one or more openings (apertures) in semiconductor layers, which can then be filled with metal to form conductive lines and/or conductive plugs.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its purpose is merely to present some concepts of the invention in a simplified form as a prelude to the more detailed description that is presented later.

According to one or more aspects of the present invention, a system facilitates monitoring and/or controlling a semiconductor fabrication process, including a damascene phase of the fabrication process. Scatterometry and/or ellipsometry based techniques can be employed to facilitate providing measurement signals indicative of processing characteristics, such as the thickness of a nitride layer being etched away during the fabrication process, for example. One or more fabrication components and/or operating parameters associated with the fabrication component(s) can be adjusted in response to the measurements to achieve a desired result, such as to mitigate formation of copper oxide during etching of a copper layer, for example.

By way of example, one or more etching components may be employed in a damascene phase of a semiconductor fabrication process. The process can be monitored by comparing signatures generated from light reflected off of a wafer undergoing the process to desired signatures. By comparing desired signatures to measured signatures, control data may be generated and employed to control the etching component and/or one or more operating parameters associated therewith, such as to adapt the etching process, for example. For instance, when the etching process is about to penetrate through a stop layer to a copper layer, etching chemistry can be altered (e.g., to non-oxygen band chemicals) to mitigate formation of copper oxide. As a result, more desirable etching can be achieved, resulting in more accurately formed and better performing semiconductors.

In accordance with one specific embodiment of the subject invention, a system that facilitates monitoring copper oxide formation in connection with a semiconductor fabrication process is provided. A measurement system receives data relating to a degree of copper oxide formation on a copper layer during the semiconductor process. An analysis component analyzes the data, the analysis comprising employing a probabilistic determination analysis (e.g., Bayesian belief network) in connection with determining the degree of copper oxide formation. A regulating component regulates the fabrication process based in part upon the analyzed data, the regulation employing feedback control to converge the semiconductor fabrication process to a desired state.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

BRIEF DESCRIPTION OF THE DRAWINGS

The present invention is illustrated by way of example in the accompanying figures.

FIG. 9 illustrates a perspective view of a grid mapped wafer according to one or more aspects of the present invention.

FIG. 10 illustrates plots of measurements taken at grid mapped locations on a wafer in accordance with one or more aspects of the present invention.

FIG. 11 illustrates a table containing entries corresponding to measurements taken at respective at grid mapped locations on a wafer in accordance with one or more aspects of the present invention.

DETAILED DESCRIPTION OF THE INVENTION

Figure 1:
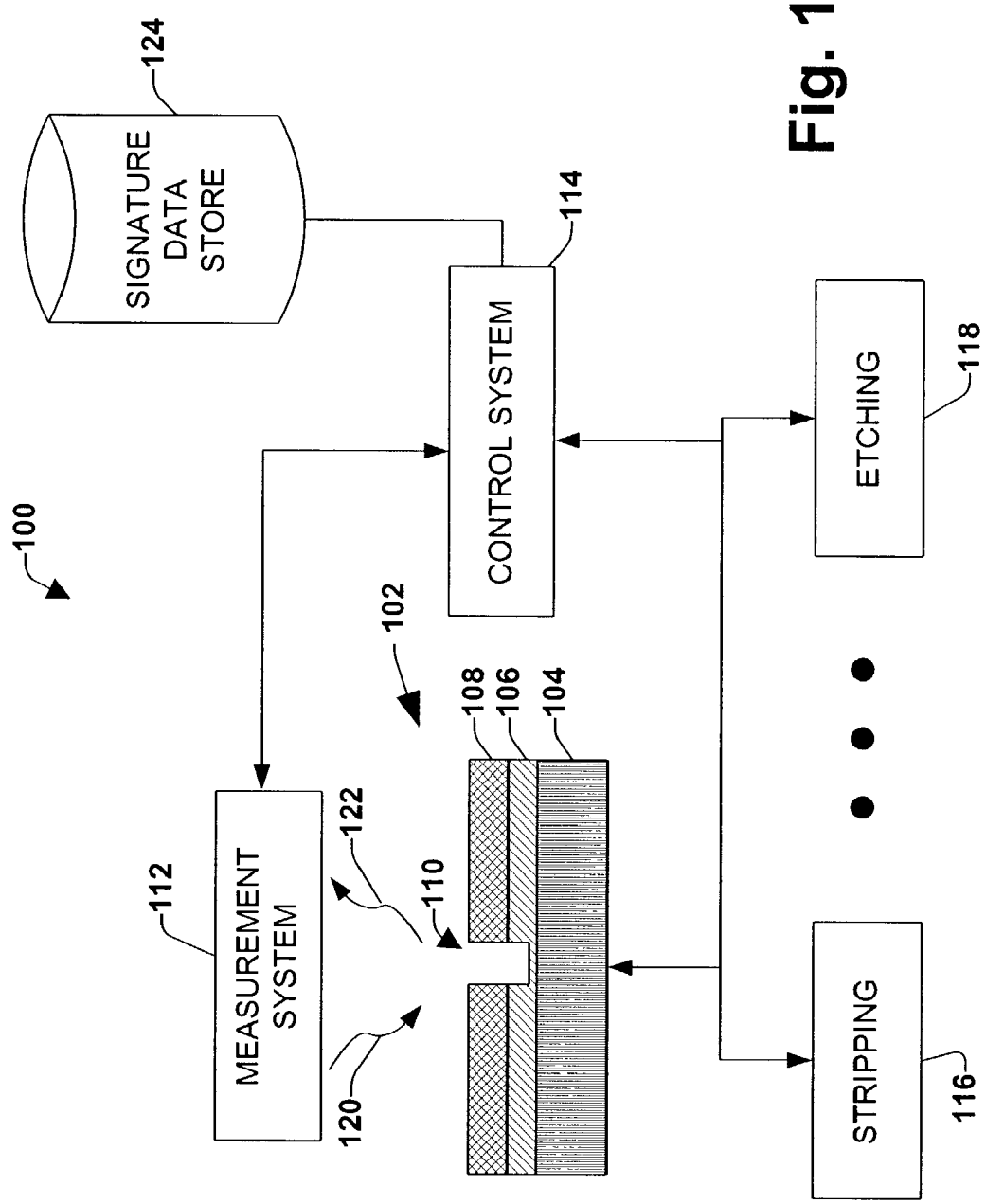
FIG. 1 is a diagramatic block representation of a system for monitoring and/or controlling a semiconductor fabrication process in accordance with one aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, to one skilled in the art that one or more aspects of the present invention may be practiced with a lesser degree of these specific details. In other instances, known structures and devices may be shown in block diagram form in order to facilitate describing one or more aspects of the present invention.

The term "component" as used herein includes computer-related entities, either hardware, a combination of hardware and software, software, or software in execution. For example, a component may be a process running on a processor, a processor, an object, an executable, a thread of execution, a program and a computer. By way of illustration, both an application running on a server and the server can be components. By way of further illustration, both a stepper and a process controlling the stepper can be components.

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed.

FIG. 1 illustrates a block diagram of system 100 for monitoring and/or controlling a semiconductor fabrication process in accordance with one or more aspects of the present invention. The system obtains measurements and collects data from a wafer 102 (or portions thereof) undergoing the fabrication process and controls the process in response to the measurements taken. The system can employ scatterometry and/or ellipsometry based techniques, for example, in obtaining the measurements. The portion of the 102 wafer illustrated in FIG. 1 may, for example, be undergoing a damascene phase of the fabrication process and is depicted as including a conductive layer 104 (e.g., copper), a stop layer 106 formed over the conductive layer 104 (e.g., for subsequent chemical mechanical polishing (CMP)) and a dielectric/insulating layer 108 formed over the stop layer. It is to be appreciated that such a stop layer 106 can, for example, be a silicon nitride, such as BLOk from Applied Materials or a layer formed from any one or more of the following (or other) chemicals: $SiH_4$, $NH_3$, $N_2$, $N_2O$, $SiH_2Cl_2$, $NH_3$, $N_2$, $N_2O$ and $Si_3N_4$; and that such an insulating layer 108 can be, for example, silicon oxide (SiO), silicon dioxide ($SiO_2$), silicon nitride ($Si_3N_4$), (SiN), silicon oxynitride ($SiO_xN_y$), fluorinated silicon oxide ($SiO_xF_y$), polysilicon, amorphous silicon, tetraethyorthosilicate (TEOS), phosphosilicate glass (PSG), borophosphosilicate glass (BPSG), any suitable spin-on glass, polyimide(s) or any other suitable dielectric material. It is to be further appreciated that while three layers are depicted on the wafer 102, the present invention has application to any number of layers formed on a wafer.

The wafer 102, and more particularly, the dielectric 108 and stop 106 layers in the wafer 102 are illustrated as having an opening or aperture 110 processed (e.g., etched) therein. Such an aperture facilitates forming a via or other desired pattern(s) in the wafer 102. It is to be appreciated that while one aperture is illustrated, many features of various shapes and sizes may be formed in the wafer 102, and that the singular aperture is merely shown for purposes of simplicity. The system 100 includes a measurement system 112 that facilitates monitoring the progress of the fabrication process by collecting data and measuring, among other things, critical dimensions (CDs) throughout the fabrication process. For example, the thickness/thinness of the layers remaining in the wafer as the aperture 110 is formed therein (e.g., via etching) can be measured by the measurement system 112. It will be appreciated that other processing parameters can also be measured, such as the width of aperture(s) and the slope of aperture(s), etc.

The system 100 also includes a control system 114 operatively coupled to the fabrication components 116, 118 and the measurement system 112. The control system 114 receives signals from the measurement system 112 indicative of measured characteristics, such as remaining layer thickness, for example. The control system 114 is programmed and/or configured to regulate the fabrication components and/or one or more operating parameters associated therewith based upon readings taken by the measurement system 112. It will be appreciated that while two fabrication components, namely stripping 116 and etching 118 are illustrated in FIG. 1, the present invention has application to fabrication processes having any number of fabrication components that can act upon the wafer throughout the fabrication process (e.g., alignment, deposition, exposing, baking, development, polishing). It will be further appreciated that a processor (not shown) may be included in the system, such as may be part of the control system, for example, to facilitate effecting the functions described herein. Such a processor, or CPU, may be any of a plurality of suitable processors, and the manner in which such a processor can be configured and/or programmed to carry out the functions described herein will be readily apparent to those having ordinary skill in the art based on the description provided herein.

The measurement system 112 operates, at least in part, by directing a beam of light 120 at the wafer 102. The incident light 120 interacts with the surface of the wafer 102 and is reinforced in certain directions and cancelled out in other directions, depending upon the topography of the wafer's surface, and is reflected 122 as complex reflected and/or refracted light. The measurement system 112 can thus include a light source (not shown) for directing a beam 120 incident to the surface of the wafer 102 and one or more light detectors (not shown) for detecting the reflected and/or diffracted light 122. It is to be appreciated that although the light 120 is illustrated being directed at one location on the wafer 102, that beam(s) of light may be directed at multiple locations on the wafer simultaneously and/or at selected portions of the wafer separately throughout the fabrication process to, for example, spot check portions of the wafer and facilitate yielding determinations such as "defect present" or "defect free" at respective locations on the wafer 102.

Various unique signatures can be produced from the light 122 reflected off of the wafer in accordance with scatterometry and/or ellipsometry based techniques, for example. Such signatures can be generated, for example, by combining phase, polarization and/or intensity information associated with the reflected light. Decisions regarding how and/or when to adapt the fabrication process can be made by comparing (e.g., by pattern matching, interpolation or otherwise) one or more signatures derived from scatterometry and/or ellipsometry based measurements to one or more scatterometry and/or ellipsometry signatures stored in a signature data store 124 operatively coupled to the control system 114, for example. As fabrication progresses, such signatures can continually be generated and employed to facilitate determining, for example, the rate at which the aperture is being formed (e.g., etched) into the layers, when the stop layer 106 will be substantially etched through, and when etching of the copper layer 104 will begin, etc. For example, at a first point in time T1, while the stop layer 106 is being etched, light reflected 122 from the stop layer 106 can be analyzed to produce a first signature S1 indicating that the dielectric layer 108 has been completely etched through, that the aperture 110 has reached a first depth D1 and that a certain percentage of the stop layer 106 has been etched away. At some subsequent point in time, light reflected 122 from the stop layer 106 can be analyzed to generate another signature S2 indicating that the aperture 110 has reached a subsequent depth D2 and that nearly all of the stop layer 106 has been etched away. Control data can be generated from such sequence analysis to maintain, increase, decrease or otherwise alter the fabrication process. For example, just as the stop layer 106 is about to be completely etched through and etching is about to begin on the copper layer 104, non-oxygen band etchant chemistry can be transitioned to to mitigate formation of copper oxide, which can have an adverse affect on resulting semiconductor devices.

By way of further example, if the stop layer 106 is etched through and formation of copper oxide is detected to such a degree that resulting circuitry would likely be rendered unsuitable for its intended purpose, then a decision can be made to discard the wafer and/or to mark it (or affected portions thereof) as unsalvageable. It will be appreciated that such a determination to discard or mark-up portions of the wafer can based upon, for example, a programmed cost-benefit analysis, Bayesian system neural network, rule based expert system, etc. For example, if it is determined that the defect can be remedied, but that the cost of doing so would outweigh the benefits received from such repair, then it could be determined that it would be more cost and time effective to simply discard the wafer 102 or designate portions thereof as unusable. If it is determined that it is not cost prohibitive to remedy the defect, the type of adjustments necessary to effect the repair can be determined. Non-linear training systems can be utilized to determine the appropriate adjustments to make, for example, to eliminate and/or retard the formation of the copper oxide, and control data can be generated therefrom. By way of example, the rate, concentration and/or volume of etchants being applied can be adjusted according to the control data. Also, once formation of copper oxide is detected, the system can, for example, be designed and configured to focus in on the trouble spot(s) to take additional measurements and obtain additional information.

In addition, the system 100 can be employed in populating the data store 124 in a training stage, for example. In a training mode, the system 100 can generate substantially unique scatterometry and/or ellipsometry signatures, which are stored in the data store 124. The data store 124 can be populated by presenting a series of wafers to the system, for instance. As such, the data store 124 can serve, for example, as a signal (signature) library that can be populated with an abundance of signatures against which one or more measurements can be compared. Alternatively, or in addition to manually observing values, simulation, modeling and/or artificial intelligence techniques can be employed to populate the data store with signatures against which measured values can be compared. It is to be appreciated that entries in the data store 124 can also, for example, be stored with/correlated with respective operating parameters under which they were obtained (e.g., illumination intensity, etchant concentration, etchant distribution volume/rate, temperature, pressure, timing parameters). As such, determinations made by comparing measurements to stored data can take into account the present value of one or more operating conditions such as temperature, pressure, etc. and the effects that these conditions are having on the fabrication process. It is to be further appreciated that the data store 124 can store data in data structures including, but not limited to one or more lists, arrays, tables, databases, stacks, heaps, linked lists and data cubes. It is also to be appreciated that many of the components of the system 100 including the data store can, for example, reside in one physical or logical device (e.g., computer, process) and/or may be distributed between two or more physical or logical devices (e.g., disk drives, tape drives, memory units). The system 100 can thus be employed to provide measurements of the fabrication processes, and to control the processes in response thereto.

Figure 2:
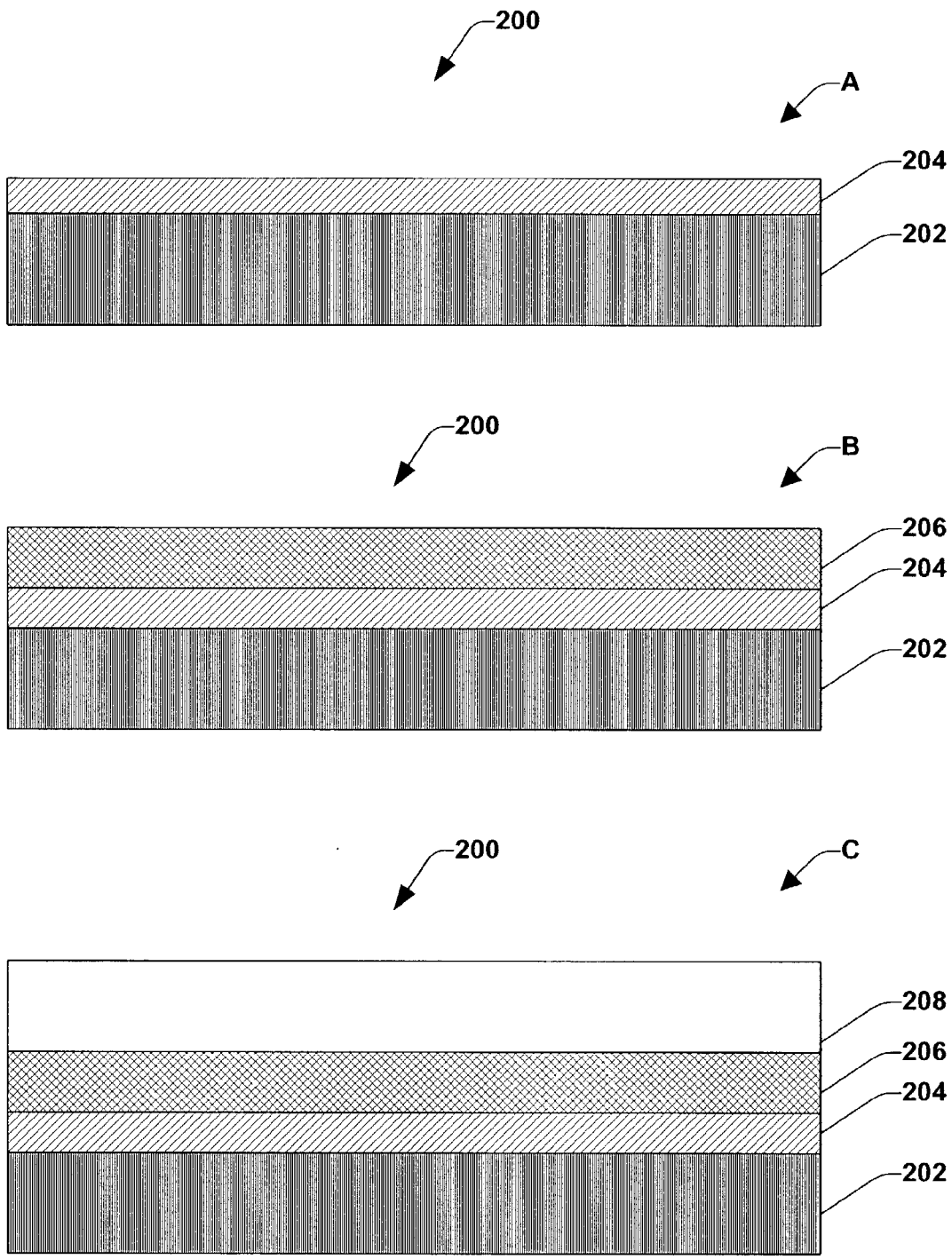
FIGS. 2–4 illustrate a portion of a wafer matriculating through various stages of a damascene phase of a semiconductor fabrication process.
Figure 3:
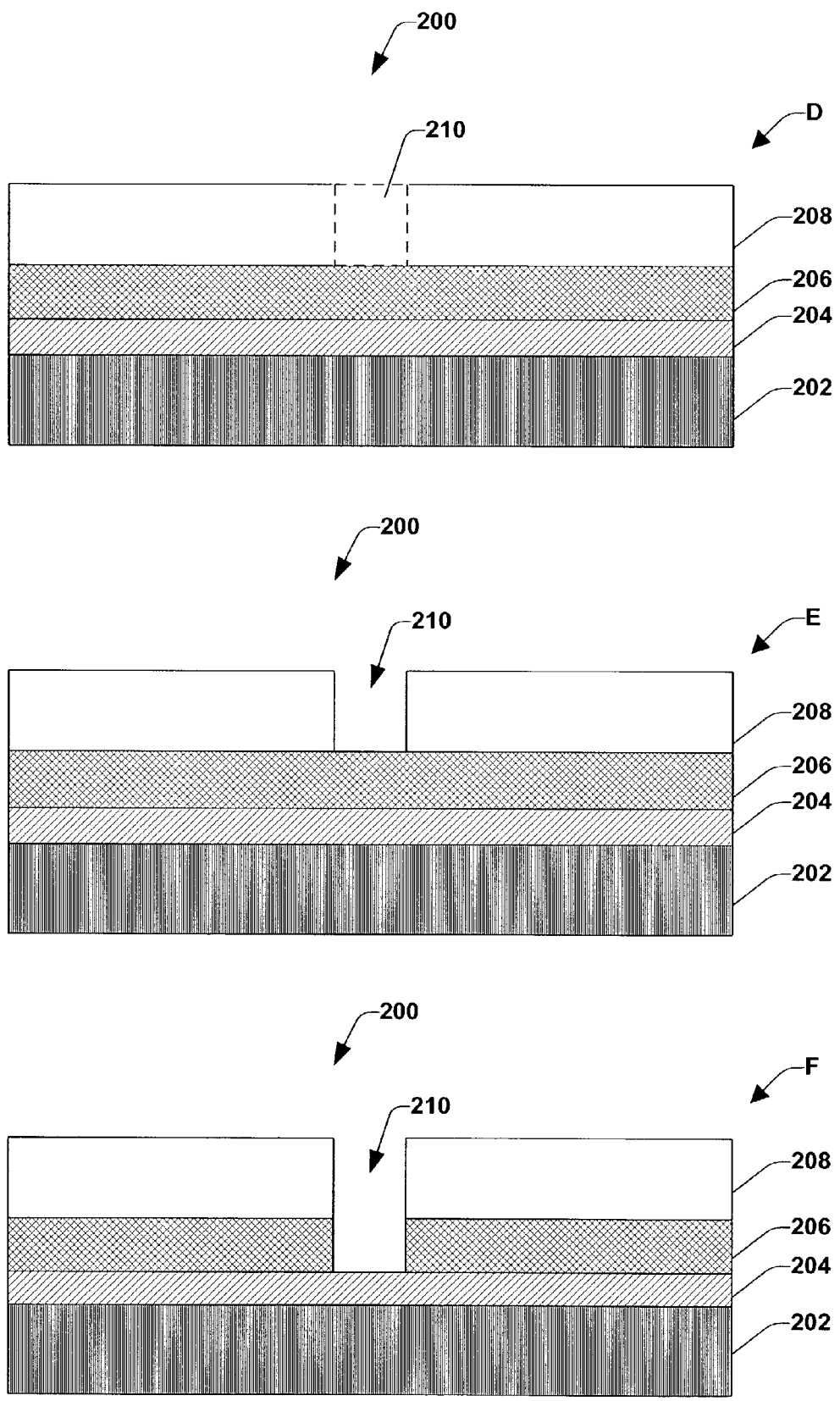
Figure 4:
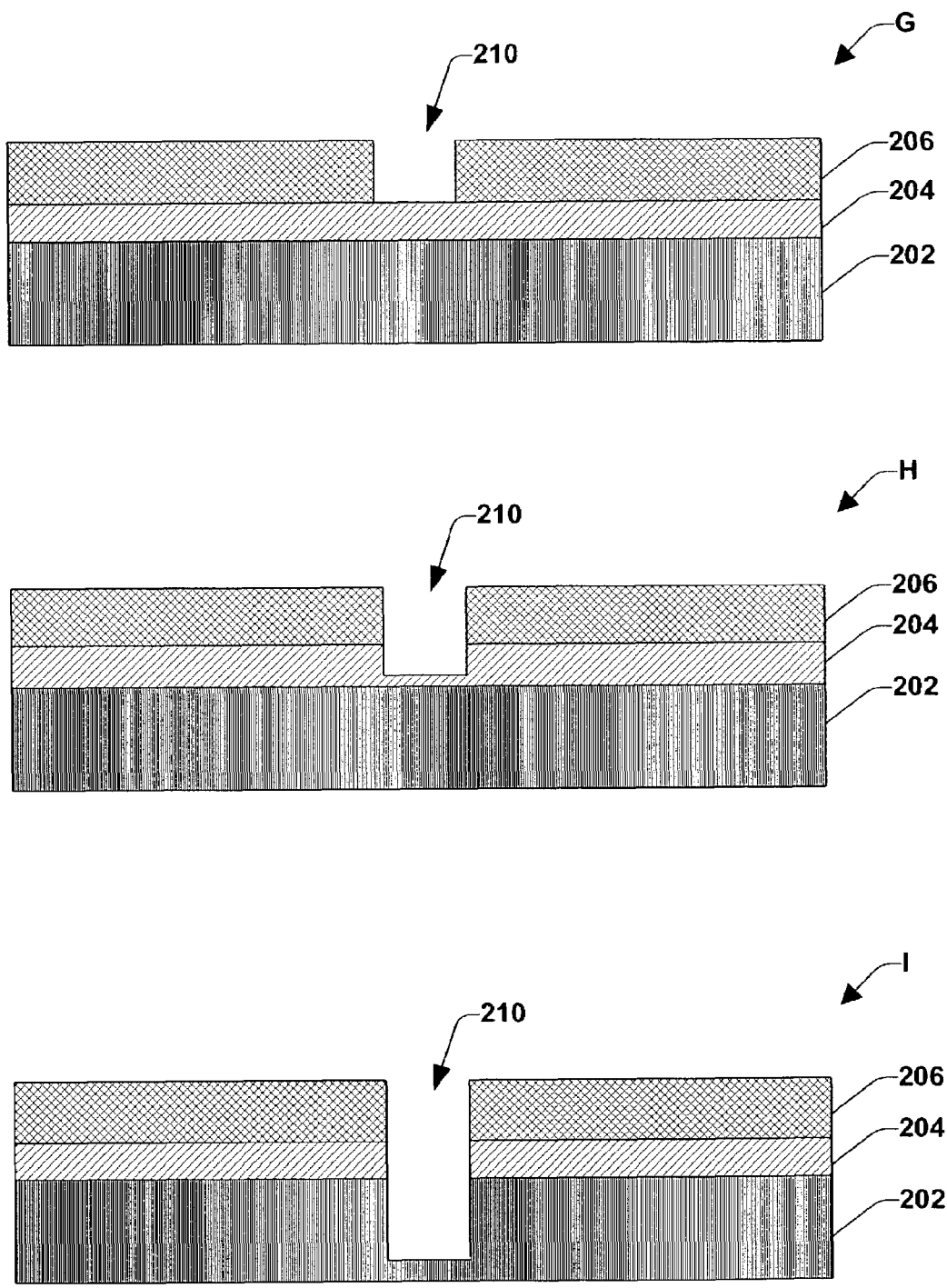

FIGS. 2–4 illustrate a wafer 200 (or a portion thereof) being transformed as it matriculates through various stages of a semiconductor fabrication process, such as may include a damascene phase of the fabrication process, for example, in accordance with one or more aspects of the present invention. At stage A, a conductive layer 202, such as a layer of copper, has a stop layer 204 (e.g., for subsequent chemical mechanical polishing (CMP)) formed thereon. The stop layer 204 can, for example, be a silicon nitride, such as BLOk from Applied Materials or $Si_3N_4$ formed from any one or more of the following (or other) gases: $SiH_4$, $NH_3$, $N_2$, $N_2O$, $SiH_2Cl_2$, $NH_3$, $N_2$ and $N_2O$. An insulating or dielectric layer 206 is formed over the stop layer at stage B. The insulating layer 206 can be, for example, silicon oxide (SiO), silicon dioxide ($SiO_2$), silicon nitride ($Si_3N_4$), (SiN), silicon oxynitride ($SiO_xN_y$), fluorinated silicon oxide ($SiO_xF_y$), polysilicon, amorphous silicon, tetraethyorthosilicate (TEOS), phosphosilicate glass (PSG), borophosphosilicate glass (BPSG), any suitable spin-on glass, polyimide(s) or any other suitable dielectric material.

A photoresist layer 208 is formed on the insulating layer 206 at stage C. The photoresist layer 208 has a thickness suitable for functioning as a mask for etching the underlying insulating layer 206 and for forming patterns or openings in the developed photoresist layer 208. By way of example, one deep UV chemically amplified photoresist is a partially t-butoxycarbonyloxy substituted poly-p-hydroxystyrene. Photoresists are commercially available from a number of sources, including Shipley Company, Kodak, Hoechst Celanese Corporation, Brewer and IBM. At stage D, the photoresist layer 208 is exposed to facilitate forming a pattern in the photoresist that includes a first opening (aperture) 210. The patterned photoresist 208 serves as an etch mask for processing or etching one or more of the underlying layers, and as such the size of the opening is about the size of an ultimate via. The patterned photoresist 208 can be formed using electromagnetic radiation having a relatively small wavelength (e.g., less than 200 nm). The photoresist layer 208 is selectively exposed to the radiation; that is, selected portions of the photoresist layer 208 are exposed to radiation. While one aperture is depicted, it is to be appreciated that the present invention has application to any number and types of features having any of a variety of sizes and shapes.

The photoresist can be either a positive or negative photoresist, and as such either the exposed or unexposed portions of the photoresist can subsequently be removed or developed, depending upon the type of resist utilized. The selectively exposed photoresist layer 208 is thus developed at stage E by contact with a suitable developer that removes either the exposed or unexposed portions of the photoresist layer 208 to form the first aperture 210 therein. The identity of the developer depends upon the specific chemical constitution of the photoresist layer 208. For example, an aqueous alkaline solution may be employed to remove portions of the photoresist layer 208. Alternatively, one or more of dilute aqueous acid solutions, hydroxide solutions, water, and organic solvent solutions may be employed to remove selected portions of the photoresist layer 208.

At stage F, the etching (e.g., anisotropic reactive ion etching (RIE)) is performed to form the via or trench 210 (e.g., that defines a pattern) in the insulating layer 206. The patterned photoresist is used as a mask for selectively etching the insulating layer 206 to provide a patterned insulating layer 206. Any suitable etching technique may be used to etch the insulating layer 206. At stage G, stripping is performed (e.g., ashing in an $O_2$ plasma or utilization of other chemical stripper) to remove remaining portions of the photoresist layer 208. The nitride stop layer 204 is then etched at stage H. The majority of the stop layer can be etched in any suitable manner, such as utilizing recipes that include $CHF_3$, $O_2$, Ar, $CF_4$, $CH_3F$ and $CH_2F_2$ to effect a dry directional etch of the stop layer 130, for example. Just as the stop layer is about to be completely etched through, however, non-oxygen band chemistry can be transitioned to so as to mitigate the formation of copper oxide. Thus, the very small amount of the remaining stop layer 204 is etched through and the via 210 is etched into the copper layer 202 to a particular depth at stage I with non-oxygen band chemistry to mitigate formation of copper oxide. It is to be appreciated that the stop layer 204 can be etched prior to stripping off the photoresist layer 208 (stage G). It will be further appreciated that the layers can be formed/deposited utilizing any number and combinatin of suitable techniques, such as, for example, spin coating, sputtering, thermal oxidation and nitridation of single crystal silicon and polysilicon, the formation of silicides by direct reaction of a deposited metal and the substrate, chemical vapor deposition (CVD), physical vapor deposition (PVD), low pressure CVD (LPCVD), plasma enhanced CVD (PECVD), high density chemical plasma vapor deposition (HDCPVD), rapid thermal CVD (RTCVD), metal organic chemical vapor deposition (MOCVD) and pulsed laser deposition (PLD).

Figure 5:
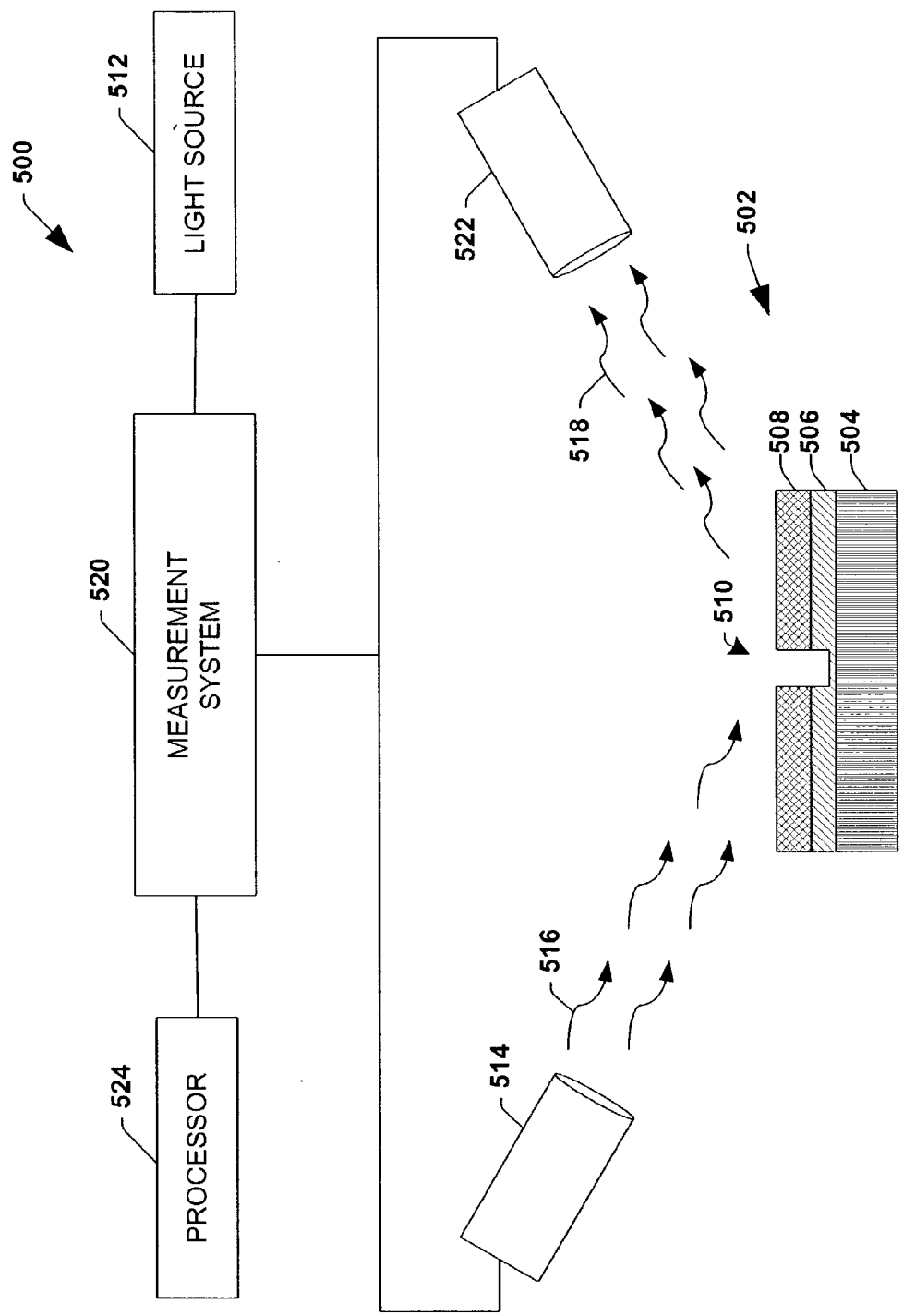
FIG. 5 is a block diagram illustrating an example of a measurement system employing scatterometry based techniques that may be utilized in accordance with one aspect of the present invention.

FIG. 5 illustrates a portion of a system 500 being employed to monitor (e.g., via scatterometry) a semiconductor fabrication process in accordance with one or more aspects of the present invention. It will be appreciated that only a small portion of a wafer 502 upon which one or more semiconductors can be fabricated is depicted in FIG. 5 for purposes of simplicity. The wafer 502 is illustrated as including a conductive layer 504 (e.g., copper), a stop layer 506 formed over the conductive layer 504 (e.g., for subsequent chemical mechanical polishing (CMP)) and a dielectric/insulating layer 508 formed over the stop layer. It is to be appreciated that such a stop layer 504 can, for example, be a silicon nitride, such as BLOk from Applied Materials or a layer formed from any one or more of the following (or other) chemicals: $SiH_4$, $NH_3$, $N_2$, $N_2O$, $SiH_2Cl_2$, $NH_3$, $N_2$, $N_2O$ and $Si_3N_4$; and that such an insulating layer 508 can be, for example, silicon oxide (SiO), silicon dioxide ($SiO_2$), silicon nitride ($Si_3N_4$), (SiN), silicon oxynitride ($SiO_xN_y$), fluorinated silicon oxide ($SiO_xF_y$), polysilicon, amorphous silicon, tetraethyorthosilicate (TEOS), phosphosilicate glass (PSG), borophosphosilicate glass (BPSG), any suitable spin-on glass, polyimide(s) or any other suitable dielectric material. An aperture 510 is illustrated as processed (e.g., etched) entirely through the insulating layer 508 and partially through the stop layer 506. It is to be appreciated that while three layers and one aperture are depicted, the present invention has application to any number of layers and any number and type of features formed therein.

A light source 512 provides light to one or more light emitters 514 that direct a light 516 incident to the wafer 502. The light 516 is reflected 518 from features in the wafer 502, including the aperture 510 formed in the wafer. The incident light 516 may be referred to as the reference beam, and thus the phase, intensity and/or polarization of the reference beam 516 may be recorded in a measurement system 520 to facilitate later comparisons to the reflected beam 518 (e.g., via signature comparison). The angle of the reflected light 518 will vary in accordance with the evolving dimensions of the aperture 510, including the decreasing thicknesses of the layers as the aperture is formed therein. Similarly, the intensity, phase and polarization properties of the specularly reflected light 518 may vary in accordance with the evolving features. One or more light detecting components 522 collect the reflected light 518 and transmit the collected light, and/or data associated with the collected light, to the measurement system 520. The measurement system forwards this information to a processor 524, which may or may not be integral with the measurement system 520. The processor 524, or central processing unit (CPU), is programmed to control and carry out the various functions described herein. The processor 524 may be any of a plurality of processors, and the manner in which the processor can be programmed to carry out the functions described herein will be readily apparent to those having ordinary skill in the art based on the description provided herein. The reflected light 518 can, for example, be analyzed to generate one or more signatures that can be compared to one or more stored signatures to facilitate determining whether the process is proceeding as planned, whether the process has reached a predetermined processing point and whether the process should be adapted. Control data can then be selectively generated and applied to adjust one or more operating parameters of one or more IC fabrication components (e.g., etching, stripping, polishing) to adapt the process and facilitate achieving a desired result. By way of example, the remaining thickness of the stop layer 506 can be determined and non-oxygen band etching chemistry can be transitioned to when the stop layer 506 is about to be etched through to mitigate the formation of copper oxide as the copper layer is etched.

Figure 6:
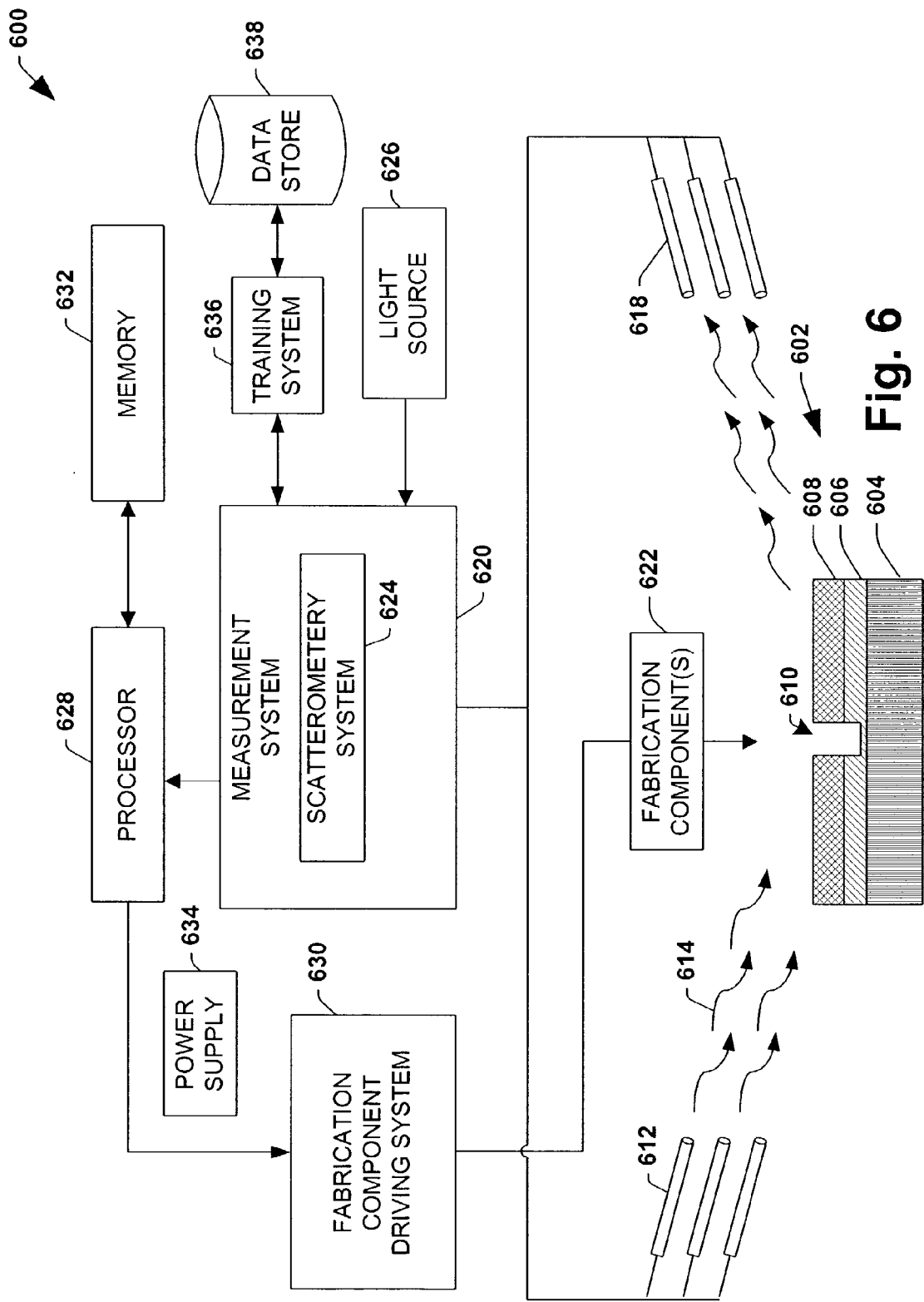
FIG. 6 is a block diagram illustrating a system for monitoring and controlling a semiconductor fabrication process via scatterometry based techniques in accordance with one or more aspects of the present invention.

Turning to FIG. 6, a system 600 for monitoring and controlling (e.g., via scatterometry) a semiconductor fabrication process according to one or more aspects of the present invention is illustrated. It will be appreciated that only a small portion of a wafer 602 upon which one or more semiconductors can be fabricated is depicted in FIG. 6 for purposes of simplicity. The wafer 602 is illustrated as including a conductive layer 604 (e.g., copper), a stop layer 606 formed over the conductive layer 604 (e.g., for a subsequent chemical mechanical polishing (CMP) step) and a dielectric/insulating layer 608 formed over the stop layer 606. It will be appreciated that such a stop layer 606 can, for example, be a silicon nitride, such as BLOk from Applied Materials or a layer formed from any one or more of the following (or other) chemicals: $SiH_4$, $NH_3$, $N_2$, $N_2O$, $SiH_2Cl_2$, $NH_3$, $N_2$, $N_2O$ and $Si_3N_4$; and that such an insulating layer 608 can be, for example, silicon oxide (SiO), silicon dioxide ($SiO_2$), silicon nitride ($Si_3N_4$), (SiN), silicon oxynitride ($SiO_xN_y$), fluorinated silicon oxide ($SiO_xF_y$), polysilicon, amorphous silicon, tetraethyorthosilicate (TEOS), phosphosilicate glass (PSG), borophosphosilicate glass (BPSG), any suitable spin-on glass, polyimide(s) or any other suitable dielectric material. An aperture 610 is illustrated as processed (e.g., etched) entirely through the insulating layer 608 and partially through the stop layer 606. It is to be appreciated that while three layers and one aperture are depicted, the present invention has application to any number of layers having any of a variety of features formed therein.

One or more light sources 612 project light 614 onto the wafer 602, which is reflected 616 in different, quantifiable manners. Light waves reinforce each other in certain directions and cancel out in other directions, creating unique signatures for different wavelengths and/or angles of incidence of the light directed onto the wafer 602. The dimensions (e.g., depth, width) of features, such as the aperture 610 forming in the wafer 602, as well as the thickness of layers being process will affect the light reflected and/or refracted by the wafer. Reflected light 616 is collected by one or more light detecting components 618, and processed by a measurement system 620. The reflected light 616 may, for example, be processed to generate signatures, which can be utilized to facilitate developing control data to selectively adjust one or more fabrication components 622 and/or operating parameters associated therewith as described herein to achieve a desired result.

The measurement system 620 includes a scatterometry system 624, which can be any scatterometry system suitable for carrying out aspects of the present invention as described herein. A source of light 626 (e.g., a laser) provides light to the one or more light sources 612 via the measurement system 620. Preferably, the light source 626 is a frequency stabilized laser, however, it will be appreciated that any laser or other light source (e.g., laser diode or helium neon (HeNe) gas laser) suitable for carrying out the present invention may be employed. Similarly, any one or more light detecting components 618 suitable for carrying out aspects of the present invention may be employed (e.g., photo detector, photo diodes) for collecting the reflected light 616.

A processor 628 receives the measured data from the measurement system 620 and is programmed to control and operate the various components within the system 600 in order to carry out the various functions described herein. The processor, or CPU 628, may be integral with the measurement system 620 and can be any of a plurality of processors, and the manner in which the processor 628 can be programmed to carry out the functions described herein will be readily apparent to those having ordinary skill in the art based on the description provided herein.

The processor 628 is also coupled to a fabrication component driving system 630 that drives one or more of the fabrication components 622. The processor 628 controls the fabrication component driving system 630 to selectively control one or more of the fabrication components 622 and/or one or more operating parameters associated therewith as described herein. For example, the type, rate, concentration and/or volume of etchants applied by an etching component can be selectively adjusted at particular points in time and/or stages of development to alter the rate and degree of etching, for example, and mitigate the formation of copper oxide. The processor 628 monitors the process via the signatures generated by the reflected and/or diffracted light, and selectively regulates the fabrication process by controlling the corresponding fabrication components 622.

A memory 632 is also shown in the example illustrated in FIG. 6. The memory 632 is operable to store, among other things, program code executed by the processor 628 for carrying out one or more of the functions described herein. The memory may include, for example, read only memory (ROM) and random access memory (RAM). The RAM is the main memory into which the operating system and application programs are loaded. The memory 632 may also serve as a storage medium for temporarily storing information and data that may be useful in carrying out one or more aspects of the present invention such as, for example, targeted thickness values, dimensional profiles, etc. For mass data storage, the memory 632 may also include a hard disk drive (e.g., 50 Gigabyte hard drive).

A power supply 634 is included to provide operating power to one or more components of the system 600. Any suitable power supply 634 (e.g., battery, line power) can be employed in carrying out the present invention.

A training system 636 may also be included. The training system 636 may be adapted to populate a data store 638

(which may be comprised within the memory 632) for use in subsequent monitoring. For example, the scatterometry system 624 can generate substantially unique scatterometry signatures that can be stored in the data store 638 via the training system 636. The data store 638 can be populated with an abundance of scatterometry signatures by examining a series of wafers. Scatterometry signatures can be compared to scatterometry measurements stored in the data store 638 to facilitate generating control data that can be employed to control the fabrication process. It is to be appreciated that the data store 638 can store data in data structures including, but not limited to one or more lists, arrays, tables, databases, stacks, heaps, linked lists and data cubes. Furthermore, the data store 638 can reside on one physical device and/or may be distributed between two or more physical devices (e.g., disk drives, tape drives, memory units).

Figure 7:
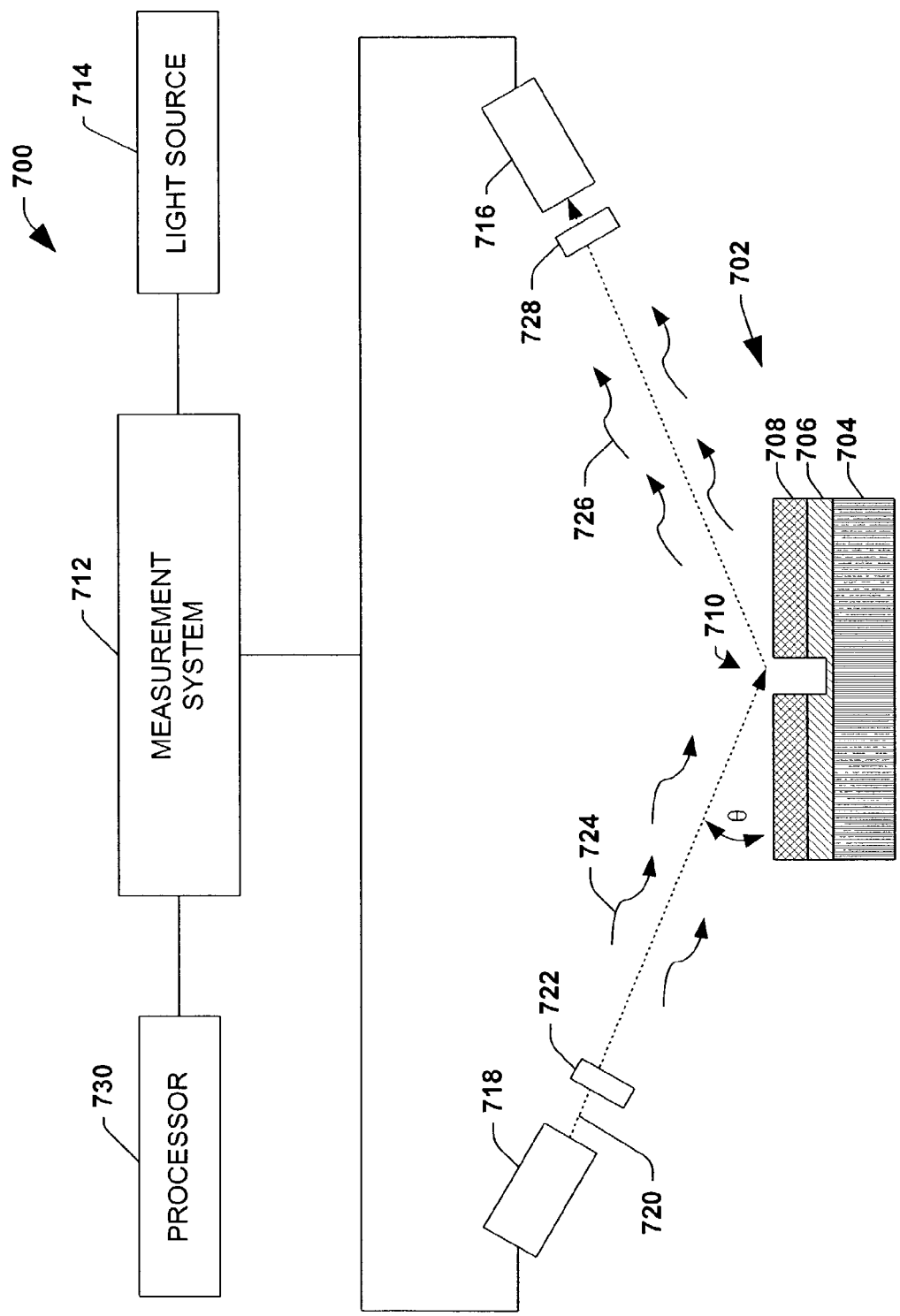
FIG. 7 is a block diagram illustrating an example of a measurement system employing ellipsometry based techniques that may be utilized in accordance with one aspect of the present invention.

FIG. 7 illustrates a portion of a system 700 being employed to monitor (e.g., via ellipsometry) a semiconductor fabrication process in accordance with one or more aspects of the present invention. Ellipsometry is a non-destructive optical technique, which deals with the measurement and interpretation state of polarized light undergoing oblique reflection from a sample surface. The quantities measured by an ellipsometer are ellipsometric angles Psi (amplitude ratio) and Delta (phase changes) which are related to the complex ratio of the Fresnel reflection coefficient Rp and Rs for light polarized parallel (p) and perpendicular (s) to the plane of incidence such that Rp/Rs=tan (PSI)$e^{iDELTA}$.

Ellipsometric data can be taken at multiple wavelengths (spectroscopic ellipsometry) and also at different angles of incidence. The experimental result of the spectroscopic variable angle of incidence ellipsometry measurements can be expressed as cos (Delta) and tan (Psi). These additional ellipsometric measurements provide much more information about the samples than can be obtained from a single wavelength and angle measurements. Spectroscopic ellipsometry is well suited for in-situ applications while spectroscopic variable angle of incidence ellipsometry allows for a more comprehensive ex-situ characterization. One type of spectroscopic ellipsometer is based on a mechanically rotating single polarizing element, polarizer (RP) or analyzer (RA). Another type is based on phase modulation (PM), where the polarizers are fixed and an additional element, the analyzer, performs the modulation function. It is to be appreciated that various types of spectroscopic ellipsometry techniques may be employed in carrying out aspects of the present invention.

It will be appreciated that only a small portion of a wafer 702 upon which one or more semiconductors can be fabricated is depicted in FIG. 7 for purposes of simplicity. The wafer 602 is illustrated as including a conductive layer 704 (e.g., copper), a stop layer 706 formed over the conductive layer 704 (e.g., for subsequent chemical mechanical polishing (CMP)) and a dielectric/insulating layer 708 formed over the stop layer 706. It is to be appreciated that such a stop layer 706 can, for example, be a silicon nitride, such as BLOk from Applied Materials or a layer formed from any one or more of the following (or other) chemicals: $SiH_4$, $NH_3$, $N_2$, $N_2O$, $SiH_2Cl_2$, $NH_3$, $N_2$, $N_2O$ and $Si_3N_4$; and that such an insulating layer 708 can be, for example, silicon oxide (SiO), silicon dioxide ($SiO_2$), silicon nitride ($Si_3N_4$), (SiN), silicon oxynitride ($SiO_xN_y$), fluorinated silicon oxide ($SiO_xF_y$), polysilicon, amorphous silicon, tetraethyorthosilicate (TEOS), phosphosilicate glass (PSG), borophosphosilicate glass (BPSG), any suitable spin-on glass, polyimide(s) or any other suitable dielectric material. An aperture 710 is illustrated as processed (e.g., etched) entirely through the insulating layer 708 and partially through the stop layer 706. It is to be appreciated that while three layers and one aperture are depicted, the present invention has application to any number of layers and any number and type of features formed therein.

A measurement system 712 is included in the system 700 and is coupled to a light source 714 and an optical detector 716. The light source 714 can be a broadband light source, such as a Xe Arc lamp or the like. The light source 714 produces a spectrum of polychromatic light over a predetermined wavelength range of interest (e.g., 100–800 nm). The light source 714 is operatively coupled (e.g. via the measurement system 712) to a lens assembly 718 comprised of one or more lenses and/or mirrors which collimate light from the light source 714. The collimated beam 720 then interacts with a polarizer 722 to create a known polarizer state. Various polarizers may be employed to carry out aspects of the present invention. The azimuth angle of the polarizer is oriented so that the plane of the electric vector associated with the linearly polarized beam 724 exiting from the polarizer 722 is at a known angle theta relative to the plane of incidence defined by the propagation direction of the beam and the normal N to the surface of the wafer 702 and the aperture etched therein.

The azimuth angle is selected, so that the reflected intensities of the P and S polarized components are approximately balanced (e.g., 25–50°). At least a portion of the beam is reflected, indicated at 726, and received at the optical detector 716. The beam 726 will have a mixed linear and circular polarization state after interacting with the etched layer(s). The reflected beam will pass through an analyzer 728, which serves to mix the polarization states incident on it. Either the polarizer 722 or the analyzer 722 is rotated, so that the detector 716 can characterize the beam. The beam enters the detector 716 which measures the intensity of the different wavelengths of light through the wavelength range of interest that pass through the analyzer 728. The detector 716 or the measurement system 712 then determines, for example, the tan (PSI) and the cos (Delta). This information is transmitted to a processor 730, which may or may not be integral with the measurement system 712. The processor 730, or central processing unit (CPU), is programmed to control and carry out the various functions described herein. The processor 730 may be any of a plurality of processors, and the manner in which the processor can be programmed to carry out the functions described herein will be readily apparent to those having ordinary skill in the art based on the description provided herein. The reflected beam 726 can, for example, be analyzed to generate one or more signatures that can be compared to one or more stored signatures to facilitate determining characteristics of the wafer, such as the remaining thickness of a layer (e.g., the stop layer 706) being etched, the depth of the aperture, the width of the aperture, etc. By way of further example, the ellipsometry system can collect measurement data substantially concurrently at spaced apart locations along the surface of the layer(s) being etched, such as at opposed side edges and a center location. The measurements made at spaced apart locations may be employed to facilitate determining uniformity of etched layers, for example. Upon determining a generally non-uniformity in layer etching, for example, control data can be selectively generated and applied to select fabrication components to adapt the process and facilitate achieving a desired result. Distribution of etchants can, for example, be selectively adjusted to facilitate uniform etching and aperture formation.

Figure 8:
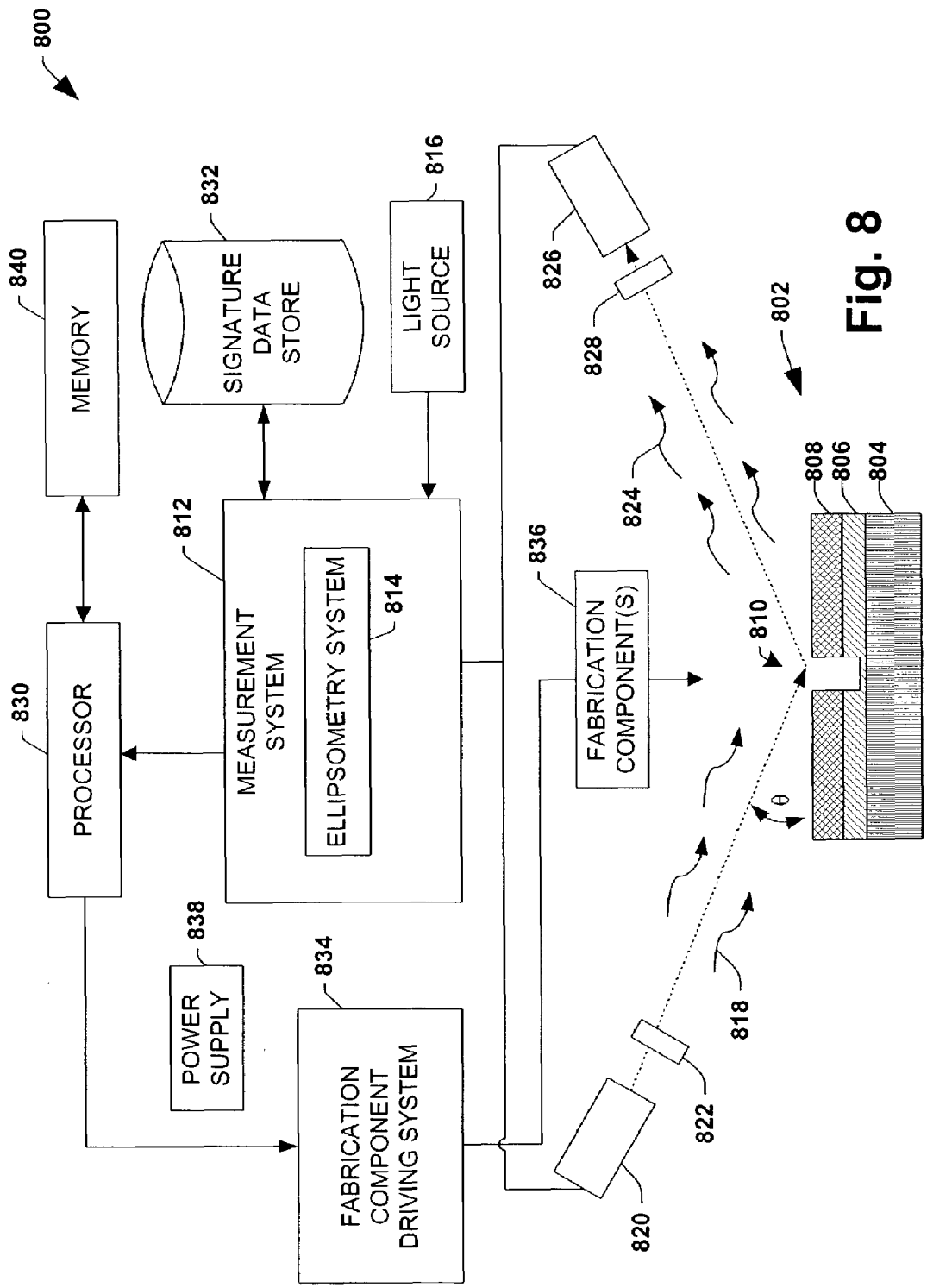
FIG. 8 is a block diagram illustrating a system for monitoring and controlling a semiconductor fabrication process via ellipsometry based techniques in accordance with one or more aspects of the present invention.

FIG. 8 illustrates a system 800 for monitoring and controlling (e.g., via ellipsometry) a semiconductor fabrication process according to one or more aspects of the present invention. It will be appreciated that only a small portion of a wafer 802 upon which one or more semiconductors can be fabricated is depicted in FIG. 8 for purposes of simplicity. The wafer 802 is illustrated as including a conductive layer 804 (e.g., copper), a stop layer 806 formed over the conductive layer 804 (e.g., for a subsequent chemical mechanical polishing (CMP) step) and a dielectric/insulating layer 808 formed over the stop layer 806. It will be appreciated that such a stop layer 806 can, for example, be a silicon nitride, such as BLOk from Applied Materials or a layer formed from any one or more of the following (or other) chemicals: $SiH_4$, $NH_3$, $N_2$, $N_2O$, $SiH_2Cl_2$, $NH_3$, $N_2$, $N_2O$ and $Si_3N_4$; and that such an insulating layer 808 can be, for example, silicon oxide (SiO), silicon dioxide ($SiO_2$), silicon nitride ($Si_3N_4$), (SiN), silicon oxynitride ($SiO_xN_y$), fluorinated silicon oxide ($SiO_xF_y$), polysilicon, amorphous silicon, tetraethyorthosilicate (TEOS), phosphosilicate glass (PSG), borophosphosilicate glass (BPSG), any suitable spin-on glass, polyimide(s) or any other suitable dielectric material. An aperture 810 is illustrated as processed (e.g., etched) entirely through the insulating layer 808 and partially through the stop layer 806. It is to be appreciated that while three layers and one aperture are depicted, the present invention has application to any number of layers with any number of features formed therein having any of a variety of shapes and sizes.

The system includes a measurement system 812 that employs an elliposometry system 814. A light source 816, such as a broadband lights source (e.g., Xe Arc lamp or the like) provides a light beam 818 (via the measurement system 812) toward the surface of the wafer 802, such as toward the nitride stop layer 806 being etched, for example. The light beam 818 from the light source 816 is collimated by a lens assembly 820 comprised of one or more lenses and/or mirrors. The beam 818 then interacts with a polarizer 822 to create a known polarizer state. At least a portion of the beam is reflected 824 and received at an optical detector 826. The beam 824 will have a mixed linear and circular polarization state as a function of the topography of the surface of the wafer 802. The reflected beam 824 will pass through an analyzer 828, which serves to mix the polarization states incident on it. Either the polarizer 822 or the analyzer 828 is rotated, so that the detector 826 can characterize the beam. The beam enters the detector 826 which measures the intensity of the different wavelengths of light through the wavelength range of interest that pass through the analyzer 828.

Information regarding the reflected beam is transmitted via the measurement system 812 to a processor 830, which may or may not be an integral component of the measurement system 812. The processor 830 receives the measurement data and is programmed to control and operate the various components within the system 800 in order to carry out the various functions described herein. It will be appreciated that the processor, or CPU 830, can be any of a plurality of processors, and the manner in which the processor 830 can be programmed to carry out the functions described herein will be readily apparent to those having ordinary skill in the art based on the description provided herein.

Using an ellipsometry technique, for example, desired information concerning layer thickness, aperture depth, aperture width, etc. can be extracted by comparing the phase and/or intensity (magnitude) of the light directed onto the surface of the wafer 802 with phase and/or intensity signals of a complex reflected and/or diffracted light resulting from the incident light reflecting from and/or diffracting through the surface of the wafer 802. The intensity and/or the phase of the reflected and/or diffracted light 824 will change based upon, among other things, the configuration of the surface of the wafer 802, such as the remaining thickness of the stop layer 806 being etched, for example.

In order to determine surface characteristics such as layer thickness, for example, measurement signals may be employed to generate a signature corresponding to the Tan (PSI) over the broadband frequency range and a signature corresponding to the Cos (Delta) over the broadband frequency range. The generated signatures may be compared with a signal (signature) library 832 of intensity/phase signatures to determine layer thickness. Such substantially unique phase/intensity signatures are produced by light reflected from and/or refracted by different surfaces due, at least in part, to the complex index of refraction of the surface onto which the light is directed.

The signal (signature) library 832 can be constructed from observed intensity/phase signatures and/or signatures generated by modeling and simulation. By way of illustration, when exposed to a first incident light of known intensity, wavelength and phase, a first feature on a wafer can generate a first component of a phase/intensity signature. Similarly, when exposed to the first incident light of known intensity, wavelength and phase, a second feature on a wafer can generate a second component of a phase/intensity signature. The components can be determined over a broadband range of wavelengths and aggregated to form a signature. For example, a layer having a first thickness may generate a first signature while a different layer or a different portion of the same layer having a different thickness may generate a second signature, which is different from the first signature.

Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing, for example, over three hundred thousand phase/intensity signatures. Thus, when the phase/intensity signals are received from ellipsometry detecting components, the phase/intensity signals can be pattern matched, for example, to the library of signals to determine whether the signals correspond to a stored signature. Interpolation between the two closest matching signatures further may be employed to discern a more accurate indication of thickness from the signatures in the signature library. Alternatively, artificial intelligence techniques may be employed to calculate desired parameters of the wafer under test based on the detected optical properties.

The processor 830 is also coupled to a fabrication component driving system 834 that drives one or more fabrication components 836. The processor 830 controls the fabrication component driving system 834 to selectively control one or more of the fabrication components 836 and/or one or more operating parameters associated therewith as described herein. For example, the type, rate, concentration and/or volume of etchants applied by an etching component can be selectively adjusted at particular points in time and/or stages of development to alter the rate and degree of etching, for example, and mitigate the formation of copper oxide.

A power supply 838 and memory 840 are also shown in the example illustrated in FIG. 8. The power supply 838 is included to provide operating power to one or more components of the system 800. Any suitable power supply 838 (e.g., battery, line power) can be employed in carrying out aspects of the present invention. The memory 840 is operable to store, among other things, program code executed by the processor 830 for carrying out one or more of the functions described herein. The memory 840 may include, for example, read only memory (ROM) and random access memory (RAM). The RAM is the main memory into which the operating system and application programs are loaded. The memory 840 may also serve as a storage medium for temporarily storing information and data that may be useful in carrying out one or more aspects of the present invention such as, for example, targeted thickness values, dimensional profiles, etc. For mass data storage, the memory 840 may also include a hard disk drive (e.g., 50 Gigabyte hard drive). It will be appreciated that the data store 832 can be included as part of the memory 840, and that the data store 832 can store data in data structures including, but not limited to one or more lists, arrays, tables, databases, stacks, heaps, linked lists and data cubes. It will be further appreciated that many of the components of the system 500 including the data store can, for example, reside in one physical or logical device (e.g., computer, process) and/or may be distributed between two or more physical or logical devices (e.g., disk drives, tape drives, memory units).

Turning now to FIGS. 9–11 a chuck 902 is shown in perspective supporting a wafer 904 whereupon one or more apertures may be formed. The wafer 904 may be logically partitioned into a grid pattern as shown in FIG. 10 to facilitate monitoring the wafer as it matriculates through a semiconductor fabrication process. Each grid block (XY) of the grid pattern corresponds to a particular portion of the wafer 904, and each grid block may have one or more apertures associated with that grid block. Portions can be individually monitored with scatterometry and/or ellipsometry based techniques for properties including, but not limited to, remaining thickness of layers being processed (e.g., etched) to form an aperture, the depth of an aperture, the width of an aperture etc. This may facilitate selectively determining to what extent, if any, fabrication adjustments are necessary. Obtaining such information may also assist in determining problem areas associated with fabrication processes.

In FIG. 10, respective plots are illustrated for measurements taken via scatterometry based techniques at portions of a wafer 904 corresponding to grid mapped locations of the wafer ($X_1Y_1 \ldots X_{12}, Y_{12}$). The plots can, for example, be signatures indicating whether copper oxide is forming on the wafer. Given the values depicted in FIG. 10, it may be determined that an undesirable condition exists at one or more locations on the wafer 904. For instance, the measurement at coordinate $X_7Y_6$ yields a plot that is substantially higher than the respective measurements of the other portions XY. This can be indicative of a defect, such as copper oxide forming at that location and/or of apertures forming outside of acceptable tolerances, such as an aperture being etched too deeply into a layer of copper. As such, fabrication components and/or operating parameters associated therewith can be adjusted accordingly to mitigate this condition. For example, non-oxygen band etching chemistry can be transitioned to to mitigate the formation of copper oxide. It is to be appreciated that although FIG. 10 illustrates the wafer 904 being mapped (partitioned) into 144 grid block portions, the wafer 904 may be mapped with any suitable number of portions to effect desired monitoring and control. Additionally, while the discussion of FIG. 10 mentions etching, it is to be appreciated that the present invention may be employed with other wafer fabrication stages, and that etching is merely illustrative, and is not intended to be limiting.

FIG. 11 illustrates a table of acceptable and unacceptable signature values. As can be seen, all the grid blocks, except grid block $X_7Y_6$, have measurement values corresponding to an acceptable value ($V_A$), while grid block $X_7Y_6$ has an undesired value ($V_U$). Thus, it has been determined that an undesirable fabrication condition exists at the portion of the wafer 904 mapped by grid block $X_7Y_6$. Accordingly, fabrication process components and parameters may be adjusted as described herein to adapt the fabrication process accordingly to mitigate the occurrence or persistence of this condition. Alternatively, the value at block $X_7Y_6$ may be indicative of an unacceptable condition such as a defect that is so significant that it warrants discarding the wafer or the affected portion of the wafer.

Figure 12:
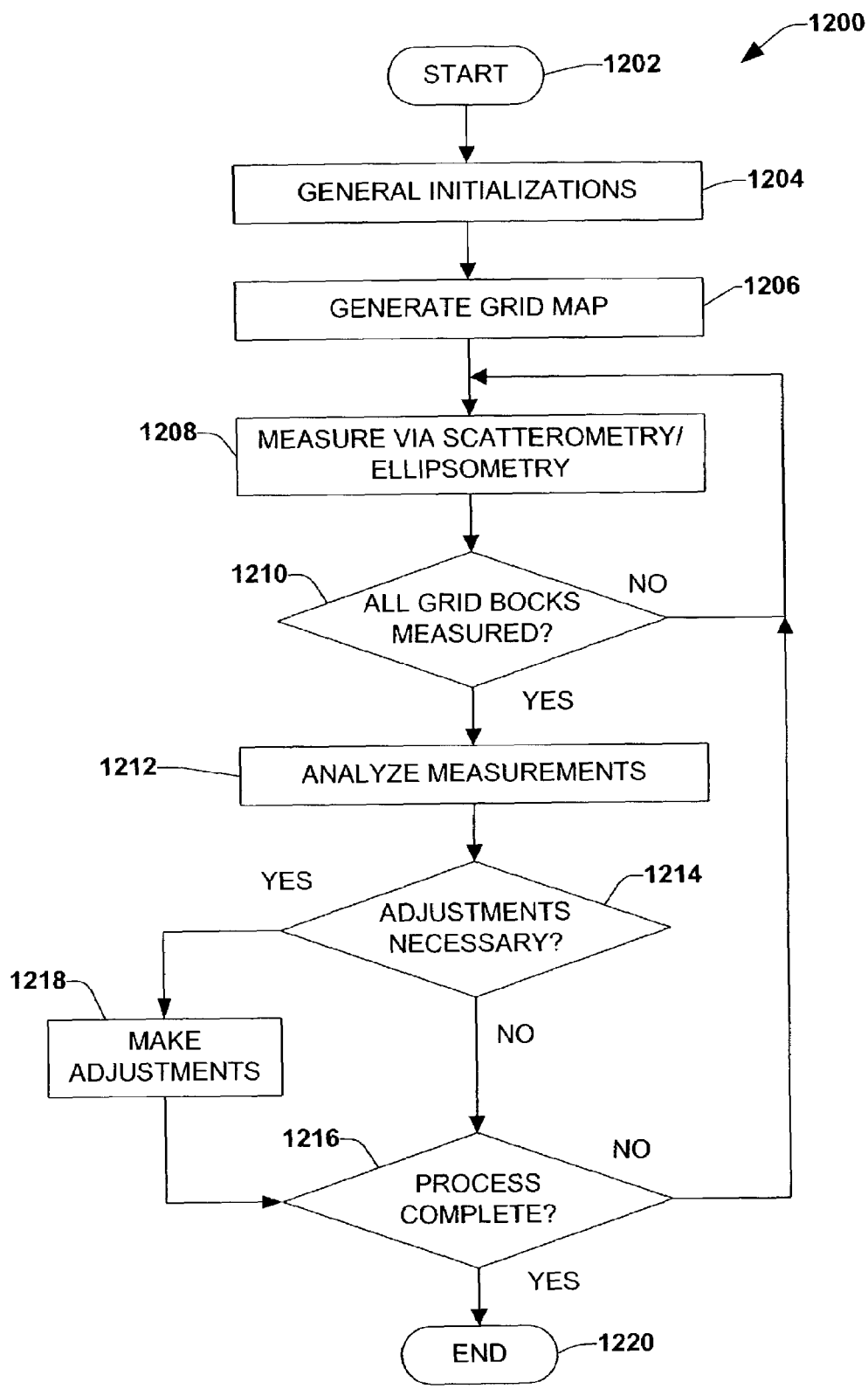
FIG. 12 is flow diagram illustrating a methodology for monitoring and controlling a semiconductor fabrication process according to one or more aspects of the present invention.

In view of the exemplary systems shown and described above, a methodology, which may be implemented in accordance with one or more aspects of the present invention, will be better appreciated with reference to the flow diagram of FIG. 12. While, for purposes of simplicity of explanation, the methodology is shown and described as a series of function blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement a methodology in accordance with one or more aspects of the present invention. It is to be appreciated that the various blocks may be implemented via software, hardware a combination thereof or any other suitable means (e.g., device, system, process, component) for carrying out the functionality associated with the blocks. It is also to be appreciated that the blocks are merely to illustrate certain aspects of the present invention in a simplified form and that these aspects may be illustrated via a lesser and/or greater number of blocks.

Turning to FIG. 12, a flow diagram illustrates a methodology 1200 for monitoring and controlling a semiconductor fabrication process according to one or more aspects of the present invention. The methodology begins at 1202 general initializations are performed at 1204. Such initializations can include, but are not limited to, establishing pointers, allocating memory, setting variables, establishing communication channels and/or instantiating one or more objects. At 1206, a grid map comprising one or more grid blocks "XY" is generated. Such grid blocks may correspond to locations on the wafer where apertures are formed, for example. At 1208, as the wafer matriculates through the fabrication process, measurements are taken at the grid mapped locations with scatterometry and/or ellipsometry based techniques. For example, the thickness of remaining layers that are being processed (e.g., etched away) during the fabrication process to form one or more apertures in the wafer can be monitored at the respective grid mapped locations. Additionally, as one or more apertures are processed (e.g., etched) into the wafer, dimensions (e.g., depth, width) of the apertures can be measured at the respective grid mapped locations. At 1210, a determination is made as to whether measurements have been taken at all (or a sufficient number) of grid mapped locations. If the determination at 1210 is NO, then processing returns to 1208 so that additional measurements can be made. At 1212, the measurements are analyzed (e.g., via a comparison of signatures generated from the measurements to stored signature values). For example, if the process is at a damascene phase, the remaining thickness of a stop layer can be analyzed to determine when the stop layer will be completely etched through and when etching will begin on an underlying copper layer, given the current rate of etching and the current composition of etchants being utilized. Additionally, measurements of aperture dimensions (e.g., depth, width) can, for example, be compared to acceptable values to determine if the fabrication process is progressing as planned. Measured values can, for example, can be compared to acceptable values to determine if, for instance, apertures are being formed within acceptable tolerances, if apertures are being formed at an acceptable rate, if material is being removed uniformly to form consistent apertures with intended planarity and configurations, etc. At 1214, a determination is made as to whether the analysis yields an indication that the process should be adjusted. For example, if a stop layer is about to be etched through in a damascene phase, it may be determined that the process should be adjusted to mitigate the formation of copper oxide on an underlying copper layer (to facilitate improved chip quality and reliability). It may be determined, for example, that non-oxygen band chemical etchants should be transitioned to right before the stop layer is about to be etched through to mitigate formation of copper oxide. Alternatively, or in addition, if an undesired value ($V_U$) is encountered it may be determined that the process should be adjusted. For example, if wafer layer(s) are being removed non-uniformly in forming an aperture, it may be determined that the distribution of etchants should be adjusted to produce an aperture with a uniform bottom, etc. Alternatively, if copper oxide is detected, it may be determined that the wafer (or the affected portions thereof) should be marked as unusable. If the determination at 1214 is NO, indicating that no adjustments are necessary, then the methodology proceeds to 1216 where a determination is made as to whether the process is over (e.g., has an aperture having a particular depth, width, etc. been completely formed). If the determination at 1216 is NO, then the methodology returns to 1208 to take additional measurements while processing continues. If the determination at 1216 is YES, indicating that processing is over, then the methodology advances to 1220 and ends. If, at 1214, the determination is YES, indicating that adjustments are necessary, then at 1218, one or more fabrications components and/or operating parameters associated therewith can be selectively adjusted as described herein to adapt the process accordingly. For example, data generated by sophisticated modeling techniques can be employed to adjust the composition of etchants applied to the wafer (e.g., to apply non-oxide band etchants to the wafer when etching is about to begin on a copper layer to mitigate formation of copper oxide). After adjustments have been made at 1218, the methodology proceeds to 1216 to see if the process is over. As mentioned above, events can occur in orders different from that depicted in FIG. 12. For example, measurements taken, as at 1208, can be analyzed, as at 1212, prior to determining whether measurements have been taken at all grid mapped locations, as at 1210.

Figure 13:
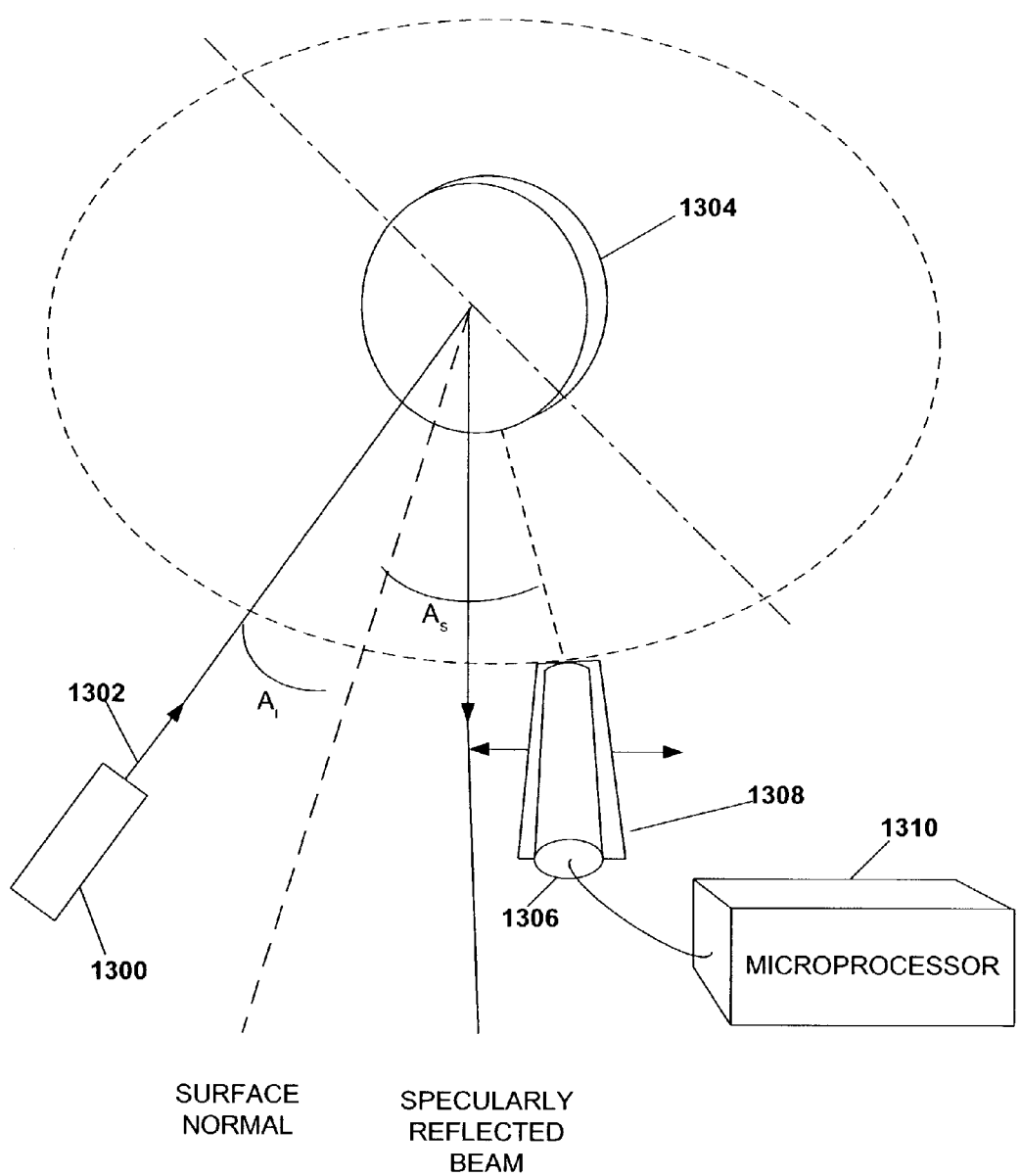
FIG. 13 illustrates an exemplary scatterometry system suitable for implementation with one or more aspects of the present invention.

FIG. 13 illustrates an exemplary scatterometry system suitable for implementation with one or more aspects of the present invention. Light from a laser 1302 is brought to focus in any suitable manner to form a beam 1304. A sample, such as a wafer 1306, is placed in the path of the beam 1304 and a photo detector or photo multiplier 1308 of any suitable construction. Different detector methods and arrangements may be employed to determine the scattered and/or reflected power. A microprocessor 1310, of any suitable design, may be used to process detector readouts, including, but not limited to, intensity properties of the specularly reflected light, polarization properties of the specularly reflected light, and angular locations of different diffracted orders. Thus, light reflected from the sample 1306 may be accurately measured.

Concepts of scatterometry and how they are employed in accordance with one or more aspects of the present invention are discussed with respect to FIGS. 14–19. Scatterometry is a technique for extracting information about a surface upon which an incident light has been directed. Scatterometry is a metrology that relates the geometry of a sample to its scattering effects. Scatterometry is based optical diffraction responses. Scatterometry can be employed to acquire information concerning properties including, but not limited to, horizontal/vertical alignment/shifting/compression/stretching, dishing, erosion, profile and critical dimensions of a surface and/or features present on a surface. The information can be extracted by comparing the phase and/or intensity of a reference light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the planarity of the surface, features on the surface, voids in the surface, the number and/or type of layers beneath the surface.

Different combinations of the above-mentioned properties will have different effects on the phase and/or intensity of the incident light resulting in substantially unique intensity/phase signatures in the complex reflected and/or diffracted light. Thus, by examining a signal (signature or stored value) library of intensity/phase signatures, a determination can be made concerning the properties of the surface. Such substantially unique intensity/phase signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$N=n-jk$, where j is an imaginary number.

The signal (signature) library can be constructed from observed intensity/phase signatures and/or signatures generated by modeling and simulation. By way of illustration, when exposed to a first incident light of known intensity, wavelength and phase, a wafer can generate a first intensity/phase signature. Observed signatures can be combined with simulated and modeled signatures to form a signal (signature) library. Simulation and modeling can be employed to produce signatures against which measured intensity/phase signatures can be matched. In one exemplary aspect of the present invention, simulation, modeling and observed signatures are stored in a signal (signature) data store. Thus, when intensity/phase signals are received from scatterometry detecting components, the intensity/phase signals can be pattern matched, for example, to the library of signals to determine whether the signals correspond to a stored signature.

Figure 14:
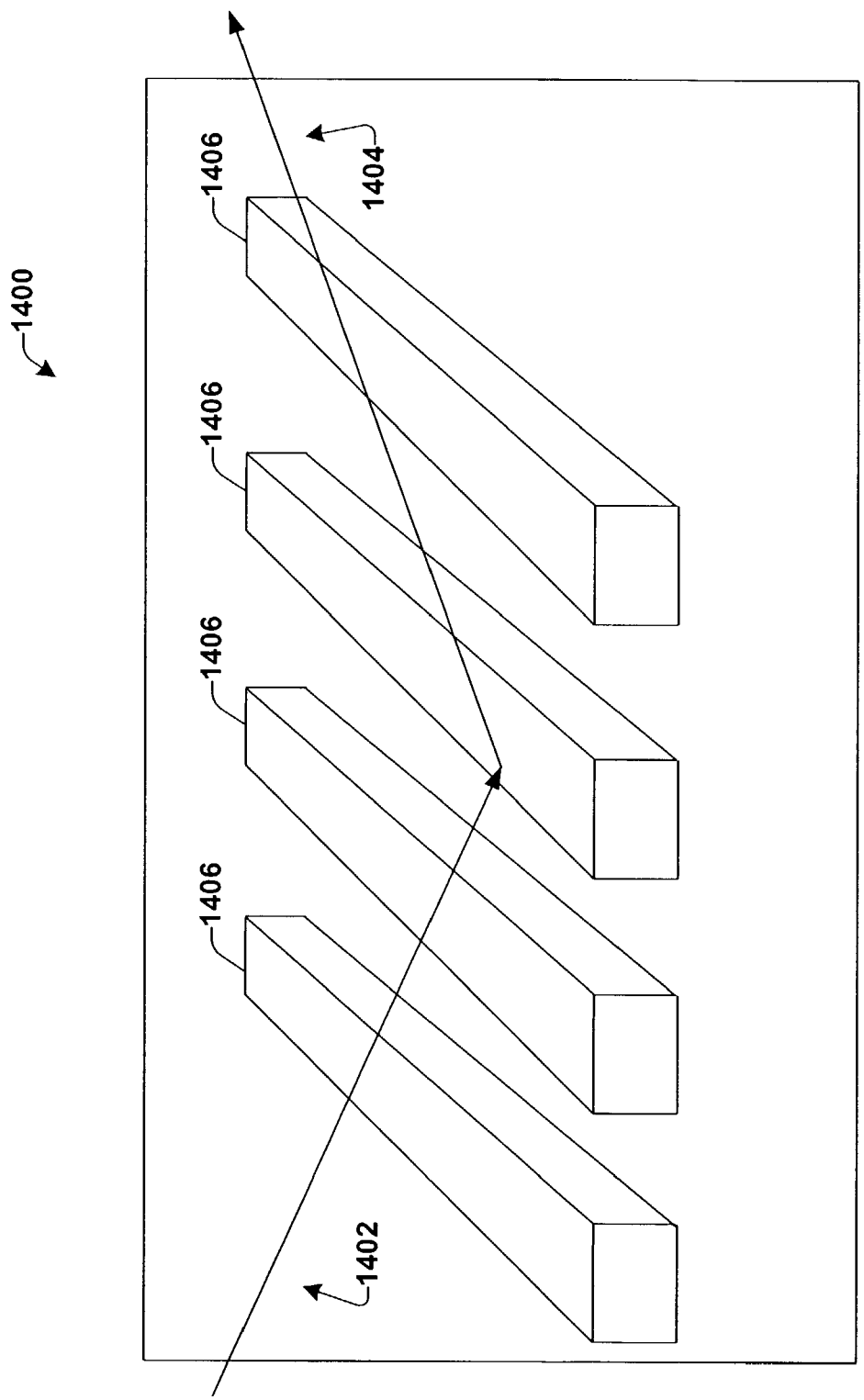
FIG. 14 is a simplified perspective view of an incident light reflecting off a surface in accordance with one or more aspects of the present invention.

To illustrate the principles described above, reference is now made to FIGS. 14 through 19. Referring initially to FIG. 14, an incident light 1402 is directed at a surface 1400, upon which one or more features 1406 may exist. The incident light 1402 is reflected as reflected light 1404. The properties of the surface 1400, including but not limited to, thickness, uniformity, planarity, chemical composition and the presence of features, can affect the reflected light 1404. The features 1406 are raised upon the surface 1400, but could also be recessed therein. The phase and/or intensity of the reflected light 1404 can be measured and plotted, as partially shown, for example, in FIG. 19. Such plots can be employed to compare measured signals with signatures stored in a signature library using techniques like pattern matching, for example.

Figure 15:
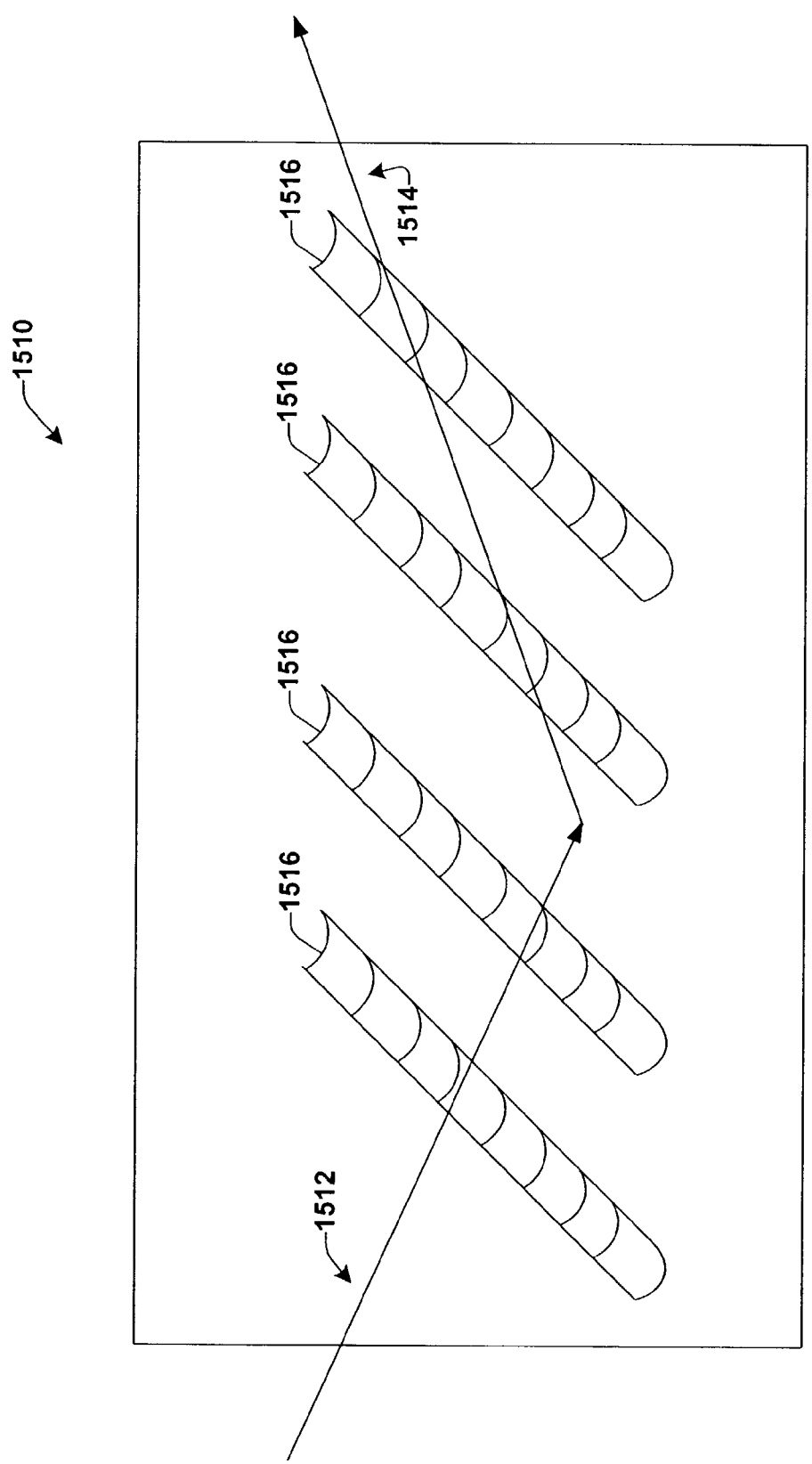
FIG. 15 is another simplified perspective view of an incident light reflecting off a surface in accordance with one or more aspects of the present invention.

Referring now to FIG. 15, an incident light 1512 is directed onto a surface 1510 upon which one or more depressions 1518 appear. The incident light 1512 is reflected as reflected light 1514. Depressions 1518 will affect the scatterometry signature to produce a substantially unique signature. It is to be appreciated that scatterometry can be employed to measure, among other things, features appearing on a surface, features appearing in a surface, features emerging in a pattern.

Figure 16:
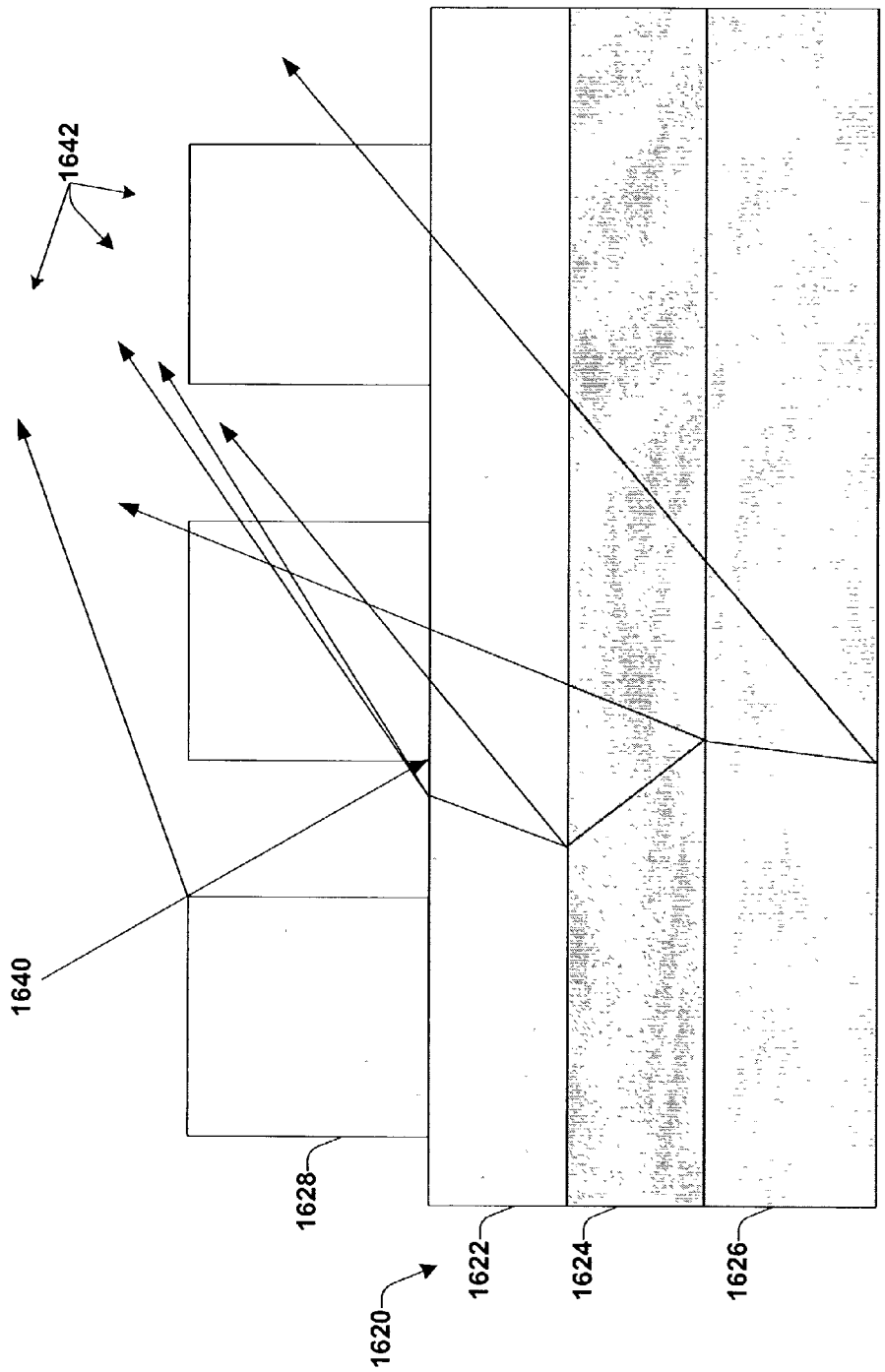
FIG. 16 illustrates a complex reflected and refracted light produced when an incident light is directed onto a surface in accordance with one or more aspects of the present invention.

Turning now to FIG. 16, complex reflections and refractions of an incident light 1640 are illustrated. The reflection and refraction of the incident light 1640 can be affected by factors including, but not limited to, the presence of one or more features 1628 and the composition of the substrate 1620 upon which the features 1628 reside. For example, properties of the substrate 1620 including, but not limited to the thickness of a layer 1622, the chemical properties of the layer 1622, the opacity and/or reflectivity of the layer 1622, the thickness of a layer 1624, the chemical properties of the layer 1624, the opacity and/or reflectivity of the layer 1624, the thickness of a layer 1626, the chemical properties of the layer 1626, and the opacity and/or reflectivity of the layer 1626 can affect the reflection and/or refraction of the incident light 1640. Thus, a complex reflected and/or refracted light 1642 may result from the incident light 1640 interacting with the features 1628, and/or the layers 1622, 1624 and 1626. Although three layers 1622, 1624 and 1626 are illustrated in FIG. 16, it is to be appreciated that a substrate can be formed of a greater or lesser number of such layers.

Figure 17:
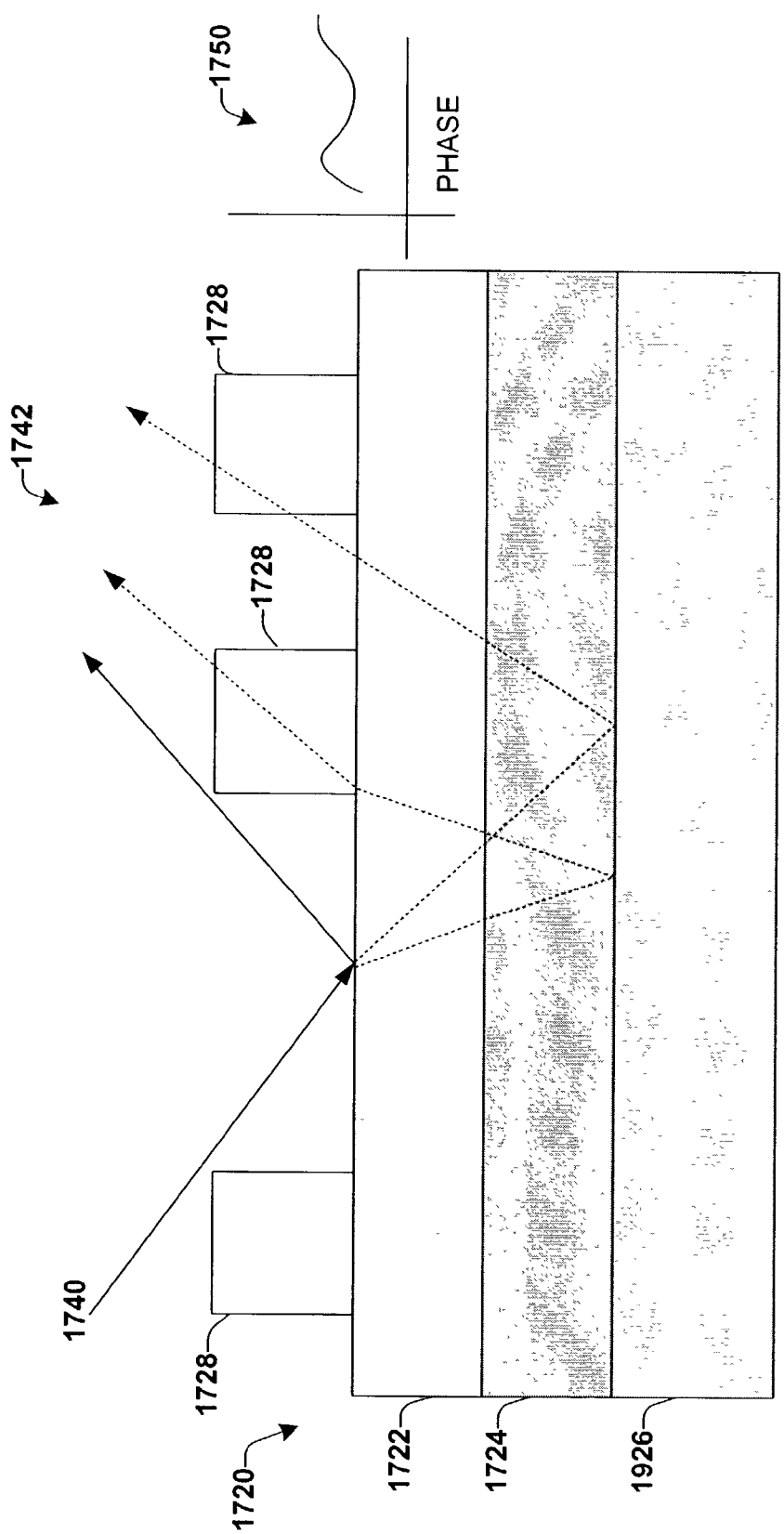
FIG. 17 illustrates another complex reflected and refracted light produced when an incident light is directed onto a surface in accordance with one or more aspects of the present invention.
Figure 18:
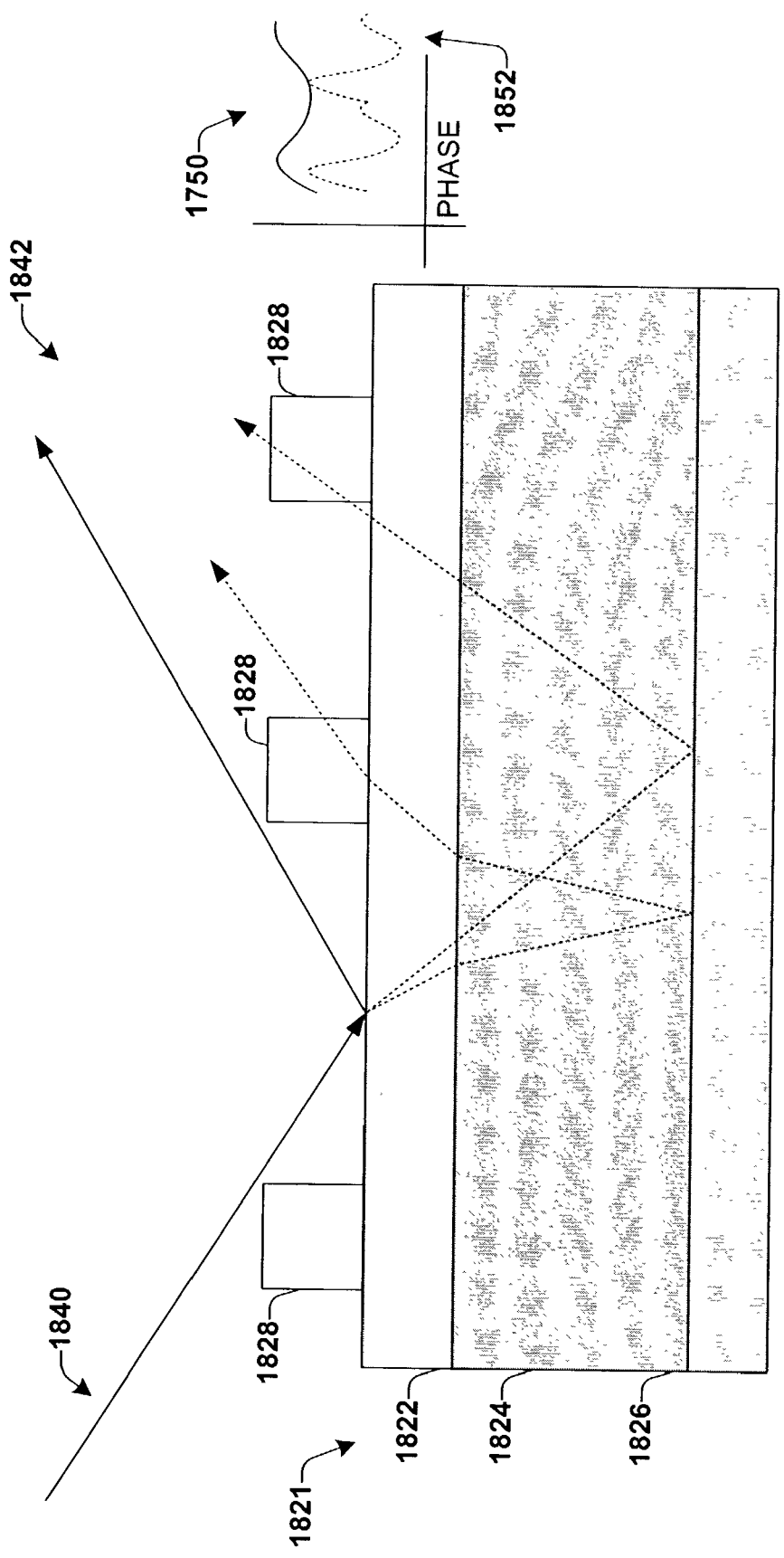
FIG. 18 illustrates yet another complex reflected and refracted light produced when an incident light is directed onto a surface in accordance with one or more aspects of the present invention.
Figure 19:
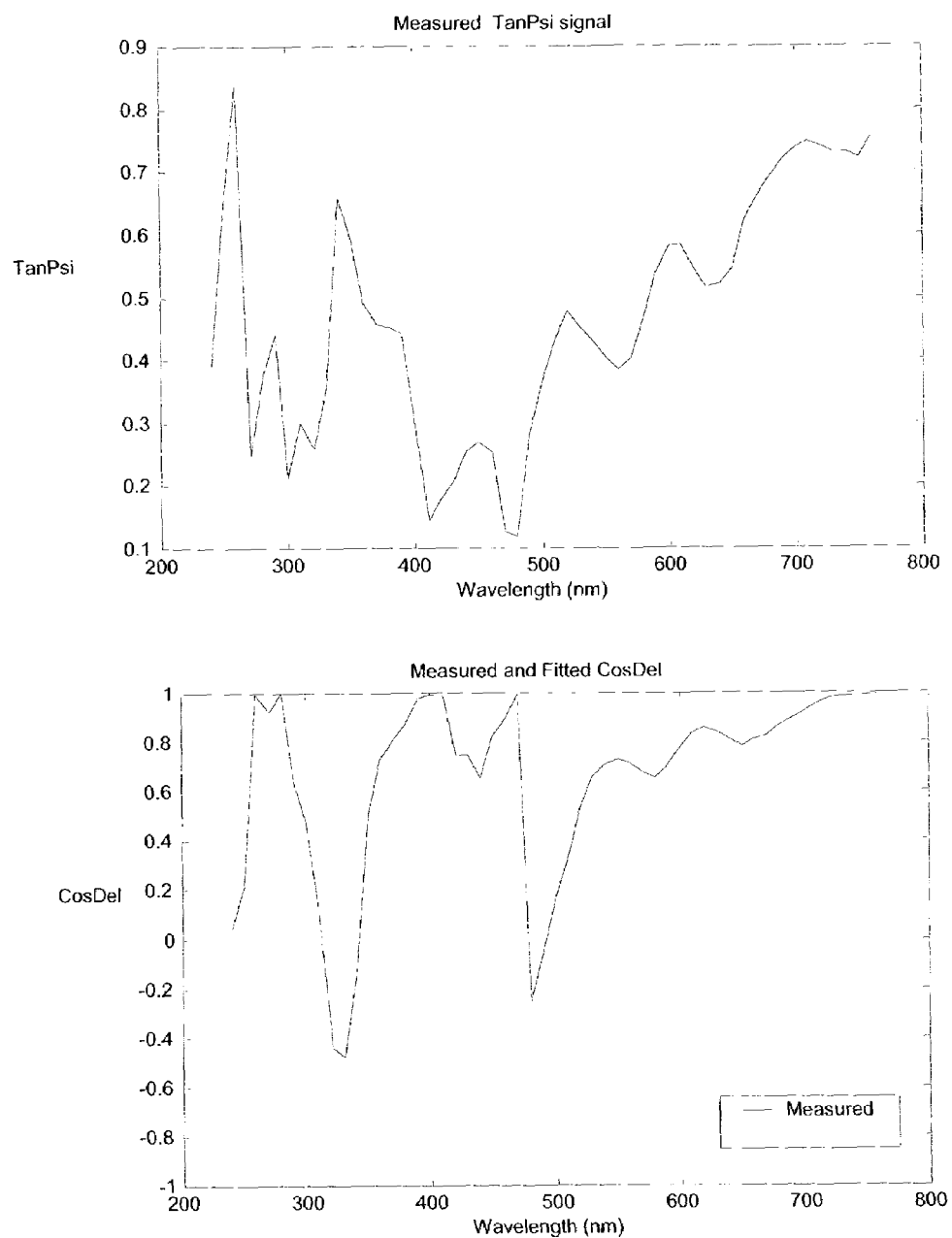
FIG. 19 illustrates phase and/or intensity signals recorded from a complex reflected and refracted light produced when an incident light is directed onto a surface in accordance with one or more aspects of the present invention.

Turning now to FIG. 17, one of the properties from FIG. 16 is illustrated in greater detail. The substrate 1720 can be formed of one or more layers 1722, 1724 and 1726. The phase 1750 of the reflected and/or refracted light 1742 from incident light 1740 can depend, at least in part, on the thickness of a layer, for example, the layer 1724. Thus, in FIG. 18, the phase 1852 of the reflected light 1842 differs from the phase 1750 due, at least in part, to the different thickness of the layer 1824 in FIG. 18.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

Using scatterometry in implementing one or more aspects of the present invention facilitates a relatively non-invasive approach to obtaining desired measurements, which can, in turn, be utilized to facilitate achieving desired results in presently occurring or subsequent processing cycles.

Although the invention has been shown and described with respect to several aspects, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including any reference to a "means") used to describe such components are intended to correspond, unless otherwise indicated, to any item(s) which performs the specified function of the described component (e.g., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A system that facilitates monitoring copper oxide formation in connection with a semiconductor fabrication process, comprising:
   a component that collects data relating to the semiconductor fabrication process;
   a system that analyzes the collected data, the analysis being based at least in part upon degree of copper oxide formation on a copper layer contained within at least a portion of a wafer undergoing the process; and
   a regulating component that regulates the fabrication process based in part upon the analyzed data and determines an appropriate time to cause a transition from an oxygen-based etching chemistry to a non-oxygen-based etching chemistry to mitigate copper oxide formation.

2. The system of claim 1, the data collecting component employing scatterometry.

3. The system of claim 1, the data collecting component employing ellipsometry.

4. The system of claim 1, the regulating component employing a feedback control methodology.

5. The system of claim 1, the analysis employing a Bayesian belief network.

6. The system of claim 1, the analysis employing a neural network.

7. The system of claim 1 wherein a semiconductor component is fabricated on the portion of the wafer during a damascene phase of the fabrication process, the component being defined at least by an aperture processed into at least a portion of the copper layer, the portion of the wafer including a stop layer formed over the copper layer, the stop layer being processed through before processing can begin on the copper layer in forming the aperture, the data collecting component measuring the thickness of the stop layer as the stop layer is processed through in forming the aperture in the wafer.

8. The system of claim 7 wherein the aperture is formed into the stop and copper layers via etching, the regulating component facilitating a transition to non-oxygen band etching chemistry as the stop layer is about to be etched through and etching is to begin on the copper layer.

9. The system of claim 8 wherein the data collecting component includes one or more light emitters that direct light incident to the wafer; and one or more light detecting components that collect light reflected from the wafer, the reflected light varying in at least one of angle, intensity, phase and polarization as the fabrication process progresses and the aperture is formed into the wafer.

10. The system of claim 9 wherein output from one or more of the light detecting components can be analyzed to generate one or more signatures for comparison to one or more stored signatures to determine the remaining thicknesses of the layers being etched.

11. The system of claim 8 wherein the data collecting component includes a broadband light source for generating a spectrum of wavelengths at the wafer;
   a polarizer to create a known polarizer state of the spectrum of wavelengths;
   an analyzer to mix the polarization states of the spectrum of wavelengths after reflection from the wafer; and
   a detector to measure the intensity of the reflected spectrum of wavelengths.

12. The system of claim 11 wherein output from the detector can be analyzed to generate a tan (PSI) signature component and cos (DELTA) signature component corresponding to the remaining thicknesses of the layers being etched.

13. The system of claim 8 wherein the stop layer comprises at least one of silicon nitride, BLOk, $SiH_4$, $NH_3$, $N_2$, $N_2O$, $SiH_2Cl_2$, $NH_3$, $N_2$, $N_2O$ and $Si_3N_4$.

14. A system that facilitates monitoring copper oxide formation in connection with a semiconductor fabrication process, comprising:
   a measurement system that receives data relating to a degree of copper oxide formation on a copper layer during the semiconductor process;
   an analysis component that analyzes the data, the analysis comprising employing a probabilistic determination analysis in connection with determining the degree of copper oxide formation; and
   a regulating component that regulates the fabrication process based in part upon the analyzed data, the regulation employing feedback control to converge the semiconductor fabrication process to a desired state and causes an in-situ transition during fabrication from an oxygen-based etching chemistry to a non-oxygen-based etching chemistry to mitigate copper oxide formation.

* * * * *